US008630660B2

(12) United States Patent  
Ray et al.

(10) Patent No.: US 8,630,660 B2
(45) Date of Patent: Jan. 14, 2014

(54) MOBILE DEVICE SUPPORTED MEDICAL INFORMATION SERVICES

(75) Inventors: Sankar Ray, Sammamish, WA (US); Farooq Bari, Bothell, WA (US)

(73) Assignee: AT&T Mobility II LLC, Atlanta, GA (US)

( * ) Notice: Subject to any disclaimer, the term of this patent is extended or adjusted under 35 U.S.C. 154(b) by 421 days.

(21) Appl. No.: 13/110,067

(22) Filed: May 18, 2011

(65) Prior Publication Data

US 2012/0293322 A1    Nov. 22, 2012

(51) Int. Cl.
    *H04W 24/00*    (2009.01)
(52) U.S. Cl.
    USPC ............................................. 455/456.3
(58) Field of Classification Search
    USPC ............................................. 455/456.3
    See application file for complete search history.

(56) References Cited

U.S. PATENT DOCUMENTS

| 5,519,760 | A  | * | 5/1996  | Borkowski et al. ........ 455/404.2 |
| 5,874,914 | A  |   | 2/1999  | Krasner |
| 6,965,576 | B1 |   | 11/2005 | Lee et al. |
| 7,366,523 | B2 |   | 4/2008  | Viikari et al. |
| 7,630,721 | B2 |   | 12/2009 | Ortiz |
| 8,428,867 | B2 |   | 4/2013  | Ashley, Jr. et al. |
| 8,483,752 | B2 |   | 7/2013  | Brisebois et al. |
| 2002/0016719 | A1 |   | 2/2002 | Nemeth et al. |
| 2008/0112551 | A1 |   | 5/2008 | Forbes et al. |
| 2013/0120133 | A1 |   | 5/2013 | Hicks, III |

FOREIGN PATENT DOCUMENTS

| WO | 2008008688 A1 | 1/2008 |
| WO | 2011106563 A1 | 9/2011 |

OTHER PUBLICATIONS

Bates, Regis J. "BUD", GPRS General Packet Radio Service, 2002, pp. 100-152, Chapters 4-5, McGraw-Hill, US.

* cited by examiner

*Primary Examiner* — Temica M Beamer
*Assistant Examiner* — Joel Ajayi
(74) *Attorney, Agent, or Firm* — Toler Law Group, PC

(57) ABSTRACT

A wireless telecommunications system can receive position information associated with a wireless mobile device of a user and a medical access point name from the wireless mobile device, can determine a gateway based on the position information and the access point name, can receive medical information associated with the user from the wireless mobile device via the gateway, and can provide, based on the medical information and the position information, the medical information to a computer system of a medical facility. The medical information can include drug allergies, food allergies, health issues, physician contact information, emergency contact information, and/or a preferred medical facility, among others. The medical information can be useful in providing medical aid to the user of the wireless mobile device if the user is not able to communicate via verbal means, via written means, and/or via sign means.

20 Claims, 14 Drawing Sheets

MOBILE DEVICE SUPPORTED MEDICAL INFORMATION SERVICES

BACKGROUND

1. Technical Field

This disclosure relates generally to the field of wireless mobile devices that deliver medical information, and, more specifically, this disclosure pertains to the field of providing medical information of a user of a wireless mobile device to a health care professional or facility via the wireless mobile device.

2. Description of the Related Art

In the past, a wireless mobile device stored information associated with its user. For example, the wireless mobile device stored information such as an address book, phone numbers of contacts, songs, a schedule, pictures, motion pictures, email, personal memos, voice memos, etc. However, a wireless mobile device did not store medical information of its user in a secure fashion, nor was it capable of securely communicating the medical information of its user to a medical professional or medical facility.

BRIEF DESCRIPTION OF THE DRAWINGS

The preferred embodiment(s) will become apparent upon reading the following detailed description and upon reference to the accompanying drawings in which.

Figure 1:
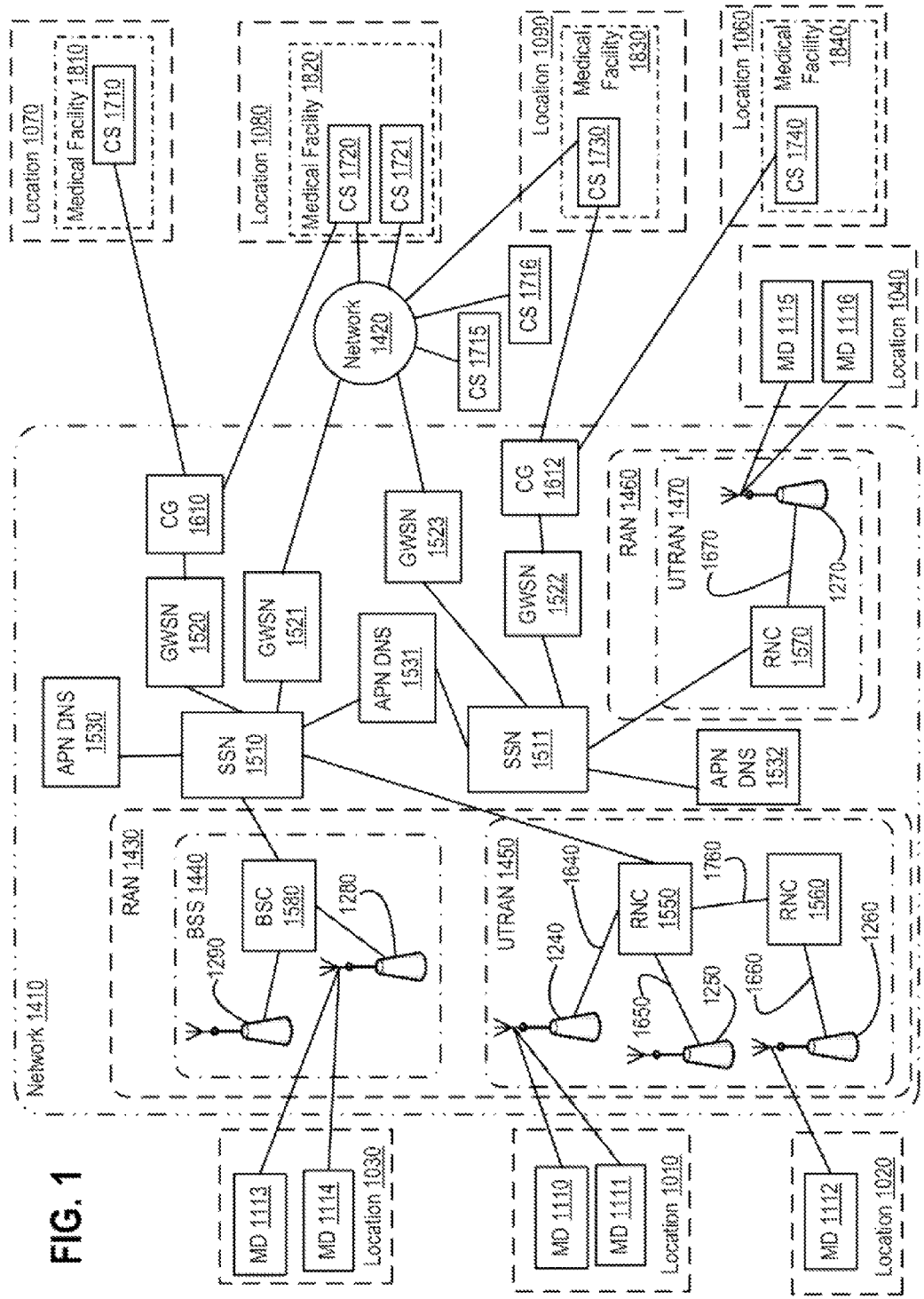
FIG. 1 provides a block diagram of one or more network communications systems, according to one or more embodiments.

While the described embodiments may be susceptible to various modifications and alternative forms, specific embodiments thereof are shown by way of example in the drawings and will herein be described in detail. It should be understood, however, that the drawings and detailed description thereto are not intended to limit the disclosure to the particular form disclosed, but on the contrary, the disclosure is to cover all modifications, equivalents and alternatives falling within the spirit and scope of an invention as defined by appended claims.

DETAILED DESCRIPTION

In one or more embodiments, a mobile device of a user can store medical information associated with the user and can provide the medical information to a medical professional and/or a medical facility. For example, the medical information can include a drug allergy, a food allergy, a health issue, physician contact information, emergency contact information, medication information, photographic information, sex, age, height, weight, health insurance information, a preferred medical provider facility, a medical provider in an insurance network, and/or an image of the user of the mobile device that can be used to identify the user, among others. This medical information can be useful in providing medical aid to the user of the mobile device if the user is not able to communicate via verbal means, via written means, and/or via sign means. In one example, the user may be unconscious or otherwise incapacitated. In a second example, the user may be unable to speak, write, or sign (e.g., using sign language) in a fashion that correctly conveys medical information. In another example, a language barrier can exist between the user and a medical provider. For instance, the user may speak, write, or sign using one language while the medical provider may speak, write, or sign using another language.

In one or more embodiments, the mobile device can interface with a near field communication device used by a medical professional (e.g., a paramedic, a nurse, a doctor, etc.) and can provide the medical information of its user to the medical professional. For example, the medical professional can use a near field device terminal to retrieve a drug allergy, a food allergy, a health issue, physician contact information, emergency contact information, medication information, sex, age, height, weight, health insurance information, a preferred medical provider facility, a medical provider in an insurance network, and/or an image of the user of the mobile device that can be used to identify the user, among others, from the user's mobile device. For instance, the mobile device can authenticate the near field device terminal before providing any medical information to the near field device terminal. Authenticating a device seeking access to the medical information can protect the user's privacy.

In one or more embodiments, the mobile device can interface with one or more computer systems of a medical facility and can provide the medical information of its user to the one or more computer system of the medical facility. For example, the mobile device can provide the medical information of its user to the medical facility before the user arrives at the medical facility. In one instance, this can facilitate and/or expedite providing medical care to the user when the user arrives at the medical facility. In another instance, this can reduce or eliminate one or more possible errors in information transmission in an emergency or non-emergency scenario.

In one or more embodiments, routing of the medical information can be provided to a nearest and/or preferred medical facility. In one example, the mobile device can provide a medical access point name (APN) and position information of the mobile device (e.g., location information of the mobile device) to a serving support node (SSN), and the SSN can query a domain name service to determine gateway servicing node (GWSN) from two or more gateway servicing nodes (GWSNs) based on the medical APN and the position information of the mobile device. In one or more embodiments, the medical APN can include a string of characters. For example, the string of characters can include "medical.local", "hospital", "office.doctor", "medical", "office.immediate-care.com", or "emergency.hospital.com", among others. In one or more embodiments, the GWSN can couple a coordination gateway to the mobile device, can receive position information (e.g., location information) associated with the mobile device, can receive, from the mobile device, medical information, associated with the user of the mobile device, and can receive information from one or more medical facilities to determine a medical facility to connect the mobile device and/or to provide the medical information associated with the user.

Turning now to FIG. 1, a block diagram of one or more network communications systems is illustrated, according to one or more embodiments. In one or more embodiments, a network 1410 can be and/or implement a telecommunications network, such as a mobile telecommunications network. In one example, network 1410 can include and/or implement a wireless telecommunications network that can support one or more wireless telecommunications network protocols such as one or more of General Packet Radio Service (GPRS), enhanced data rates for GSM (global system for mobile communications) evolution (EDGE), long term evolution, (LTE), CDMA (code division multiple access), TDMA (time division multiple access), and FDMA (frequency division multiple access), among others. In another example, network 1410 can be coupled to a public switched telephone network (PSTN). For instance, one more of radio network controllers (RNCs) 1550 and 1570 and a base station controller (BSC) 1580 can be coupled to a PSTN.

In one or more embodiments, network 1410 can be coupled to and/or include a telephony network that can include a wireless cellular telecommunications network and/or a wireless satellite telecommunications network. In one or more embodiments, the telephony network can communicate information such as voice and/or data. In one or more embodiments, network 1410 can implement, provide access to, and/or provide services of one or more other networks. In one example, network 1410 can provide access to and/or services of a public network (e.g., the Internet) to one or more of MDs 1110-1116. In another example, network 1410 can provide access to and/or services of network 1420 and/or a network coupled to network 1420.

As shown, network 1410 can include a radio access network (RAN) 1430 that can include a base station subsystem (BSS) 1440. As illustrated, BSS 1440 can include a base station controller (BSC) 1580 and one or more base transceiver stations BTSes 1280 and 1290 that can be coupled to BSC 1580. In one or more embodiments, a base transceiver station (BTS) can include one or more transmitters, one or more receivers, one or more transceivers, one or more antennas, and/or one or more cryptography devices that can be used to communicate with one or more MDs 1113 and 1114 and BSC 1580. For example, the one or more transmitters, the one or more receivers, and/or the one or more transceivers of a BTS can communicate via a layer one of an air interface (e.g., a wireless interface). In one or more embodiments, one or more antennas of the BTS can be mounted on a roof of a building, on a mast, on a tower (e.g., a cellular telephone communications tower), and/or on a side of a structure (e.g., a building, a parking garage, a lamp post, etc.). In one or more embodiments, position information associated with the one or more antennas of the BTS can be utilized in determining position information associated with a MD communicating with the BTS. As illustrated, BSC 1580 can be coupled to a SSN 1510. In one or more embodiments, SSN 1510 can be or include a servicing GPRS support node (SGSN).

As shown, RAN 1430 can include a universal mobile telecommunications system (UMTS) terrestrial radio access network (UTRAN) 1450, and a RAN 1460 can include a UTRAN 1470. As illustrated, UTRAN 1450 can include one or more RNCs 1550 and 1560, one or more node Bs (NBs) 1240 and 1250 coupled to RNC 1550, and/or node B (NB) 1270 coupled to RNC 1570 which can be coupled to RNC 1550. As shown, NBs 1240 and 1250 can be coupled to RNC 1550 via respective data communication paths 1640 and 1650. In one or more embodiments, a data communication path coupling a RNC to a NB, such as data communication path 1640, can be referred to as an Iub interface. As illustrated, a RAN 1460 can include a UTRAN 1470 that can include a RNC 1570 and a NB 1270 which can be coupled to RNC 1570.

In one or more embodiments, a data communication path that couples a NB to a RNC can include one or more wired connections. In one example, the data communication path that couples the NB to the RNC can include one or more of metallic cables and fiber optic cables that can respectively convey electromagnetic signals and optical signals. In one example, the data communication path that couples the NB to the RNC can include one or more of a T1, an E1, a T3, an E3, an OC-3, and an OC-12, among others. As shown, NB 1270 can be coupled to a RNC 1570, and NB 1260 can be coupled to a RNC 1560 which can be coupled to RNC 1550 via a data communication path 1760.

In one or more embodiments, a NB can denote include a base transceiver station in a UMTS and can include one or more transmitters, one or more receivers, one or more transceivers, and/or one or more antennas. In one example, a NB can utilize a wideband code division multiple access (WCDMA) and/or a time division synchronous code division multiple access (TD-SCDMA) in implementing an air interface (e.g., wireless interface) with one or more mobile devices. In another example, a NB can be controlled by a RNC (e.g., NB 1240 can be controlled by RNC 1550). In one or more embodiments, one or more antennas of the NB can be mounted on a roof of a building, on a mast, on a tower (e.g., a cellular telephone communications tower), and/or on a side of a structure (e.g., a building, a parking garage, a lamp post, etc.). In one or more embodiments, position information associated with the one or more antennas of the NB can be utilized in determining position information associated with a MD communicating with the NB. As illustrated, RNC 1550 can be coupled to SSN 1510, and RNC 1570 can be coupled to a SSN 1511.

In one or more embodiments, RNC 1550 and/or RNC 1570 can be coupled to one or more of a core network circuit switched domain and a core network packet switched domain. For example, RNC 1550 and/or RNC 1570 can communicate telephonic and/or circuit switched data via the core network circuit switched domain to a PSTN and/or can communicate packet switched data (e.g., IP (Internet protocol) data) via the core network packet switched domain to network 1420. In one or more embodiments, RNC 1560 can be coupled to RNC 1550, and RNC 1560 can communicate telephonic and/or circuit switched data with a PSTN via RNC 1550 and/or packet switched data (e.g., IP data) with network 1420 via RNC 1550. In one or more embodiments, one or more of BSC 1580, BTSes 1280 and 1290, RNCs 1550-15570, and NBs 1240-1270 can include one or more computer systems that can implement one or more systems and/or methods described herein.

In one or more embodiments, signals and/or signaling can be used in communicating establishment and/or control of communications and/or access to a network and/or resources of the network. In one or more embodiments, signals and/or signaling can be used between two different network providers or between two systems of a single network provider. In one example, a first network provider can be or include a second network provider, and signals and/or signaling can be used between the first network provider and the second network provider can mean signaling between two systems of the first network provider. In one or more embodiments, signals and/or signaling can be used to convey information (e.g., configuration messages, accounting messages, network management data, control data, etc.) that is different than user information transfer (e.g., a telephone conversation between two users, a text message communication between two users, etc.).

In one or more embodiments, network 1420 can provide access and/or services of one or more other networks to NBs 1240-1270 and/or BTSes 1280 and 1290. For exmaple, access to these networks can include one or more "services" these networks may provide. For instance, these one or more services can include one or more of: email, world wide web, file transfer, printing, file sharing, file system sharing, remote file system, network file system (NFS), news, multicast, netbios, encryption, domain name service (DNS), routing, tunneling, chat such as Internet Remote Chat and/or AOL Instant Messenger, gaming, licensing, license management, digital rights management, network time, remote desktop, remote windowing, audio, database (e.g., Oracle, Microsoft SQL Server, PostgreSQL, etc.), authentication, accounting, authorization, virtual local area network (VLAN) (e.g., IEEE 802.1q), virtual private network or VPN, audio, phone, Voice Over Internet Protocol (VoIP), paging, and video, among others. In one or more embodiments, the one or more service can be associated with and/or correspond to one or more protocols of one or more computer and/or software applications.

In one or more embodiments, network 1410 and/or network 1420 can include a wired network, a wireless network or a combination of wired and wireless networks. Network 1410 and/or network 1420 can include and/or be coupled to various types of communications networks, such as a PSTN, an Internet, a wide area network (WAN) (e.g., a private WAN, a corporate WAN, a public WAN, etc.), a local area network (LAN), etc. In one or more embodiments, a wireless access point (AP) can be coupled to network 1420, e.g., via: Ethernet cable and DSL; a cable (television) based network; a satellite-based system; and/or a fiber based network; among others. In one or more embodiments, network 1410 and/or network 1420 can include one or more wireless networks, e.g., based on IEEE (Institute of Electrical and Electronics Engineers) 802.11 and/or IEEE 802.16, among others. In one or more embodiments, network 1410 and/or network 1420 can include one or more DSL (digital subscriber line) and/or cable (e.g., cable television) networks and/or infrastructures. For example, network 1410 and/or network 1420 can include one or more of: cable modems, cable modem termination systems (CMTSs), satellite modems, DSL modems, digital subscriber line access multiplexers (DSLAMs), broadband remote access servers (BRASs), telecommunications circuits, and/or metropolitan area networks (MANs), among others. In one or more embodiments, network 1420 may form part of the Internet, or may couple to other networks, e.g., other local or wide area networks such as the Internet.

As shown, one or more BTSes 1280 and 1290 and/or NBs 1240-1270 can provide wireless voice and/or data communications services to mobile devices (MDs) 1110-1116. As illustrated, MDs 1110 and 1111 can be wirelessly coupled to NB 1240, mobile device (MD) 1112 can be wirelessly coupled to NB 1260, MDs 1115 and 1116 can be wirelessly coupled to NB 1270, and MDs 1113 and 1114 can be wirelessly coupled to BTS 1280. As illustrated, BSC 1580 and RNC 1550 can be coupled to SSN 1510, and RNC 1570 can be coupled to a SSN 1511. In one or more embodiments, SSN 1511 can be or include a SGSN.

In one or more embodiments, a MD couples to a SSN to use one or more packet data network services, and the SSN can provide one or more of authentication, authorization, accounting, and quality of service (QoS), among others, associated with the MD. In one example, the SSN can provide one or more of authentication, authorization, and accounting for a medical APN. In a second example, a MD of MDs 1110-1114 couples to SSN 1510 to use one or more packet data network services. For instance, the MD of MDs 1110-1114 couples to SSN 1510 to use services of network 1420, a medical facility 1810, or a medical facility 1820. In another example, a MD of MDs 1115 and 1116 couples to SSN 1511 to use one or more packet data network services. For instance, the MD of MDs 1115 and 1116 couples to SSN 1511 to use services of network 1420, a medical facility 1830, or a medical facility 1840.

In one or more embodiments, a SSN can receive an APN from a MD and can determine a GWSN from two or more GWSNs, based on the APN, that can be used in providing the one or more packet data network services to the MD. In one example, MD 1111 can provide an APN (e.g., an APN of "att.internet", "internet", or "internet.gprs", among others) to SSN 1510, and SSN 1510 can query an APN domain name service (DNS) 1530 to determine a GWSN 1521 that is coupled to network 1420 which can include or be coupled to an Internet. In another example, MD 1115 can provide an APN (e.g., an APN of "att.internet", "internet", or "internet.gprs", among others) to SSN 1511, and SSN 1511 can query an APN DNS 1531 to determine a GWSN 1523 that is coupled to network 1420 which can include or be coupled to an Internet. As illustrated, SSN 1510 can be coupled to APN domain name services (DNSes) 1530 and 1531, and SSN 1511 can be coupled to APN DNSes 1531 and 1532. In one or more embodiments, one or more of DNSes 1530-1532 can be utilized in determining a GWSN associated with an APN.

In one or more embodiments, a SSN can receive an APN and position information (e.g., location information or a location identification) associated with a MD, and the SSN can determine a GWSN from two or more GWSNs, based on the APN and the position information, that can be used in providing the one or more packet data network services to a MD. For instance, one or more of DNSes 1530-1532 can be utilized in determining a GWSN from two or more GWSNs associated with an APN and one or more of a location, location data, and location identifier. For example, an APN and each of locations 1010-1040 can be associated with a respective GWSN. In one instance, an APN (e.g., "medical.local") and location 1010 can be associated with GWSN 1520. In another instance, the APN (e.g., "medical.local") and location 1040 can be associated with GWSN 1522.

In one or more embodiments, an APN DNS can receive an APN and location data (e.g., location data associated with a location of locations 1010-1040) and can determine a GWSN based on the APN and the location data. In one example, a location 1010 can be included in a city (e.g., Austin, Tex.), and APN DNS 1531 can receive a medical APN and location data associated with location 1010 and can determine GWSN 1520 based on the medical APN and the location data associated with location 1010. In another example, a location 1040 can be included in a city (e.g., San Antonio, Tex.), and APN DNS 1531 can receive a medical APN and location data associated with location 1040 and can determine GWSN 1522 based on the medical APN and the location data associated with location 1040. For instance, the same medical APN can be used in Austin, Tex. and in San Antonio, Tex. and can be determined to be, respectively, GWSN 1520 and GWSN 1522. In one or more embodiments, position information associated with a MD can include location data associated with a location (e.g., a location of locations 1010-1040). For example, the location data can include one or more of a state, a city, a zip code, a street, a street number, a unit identifier (e.g., a suite identifier, a condominium identifier, an apartment identifier, etc.), a cell identification (cell ID or CID), latitude information, longitude information, and altitude information, among others.

Figure 2A:
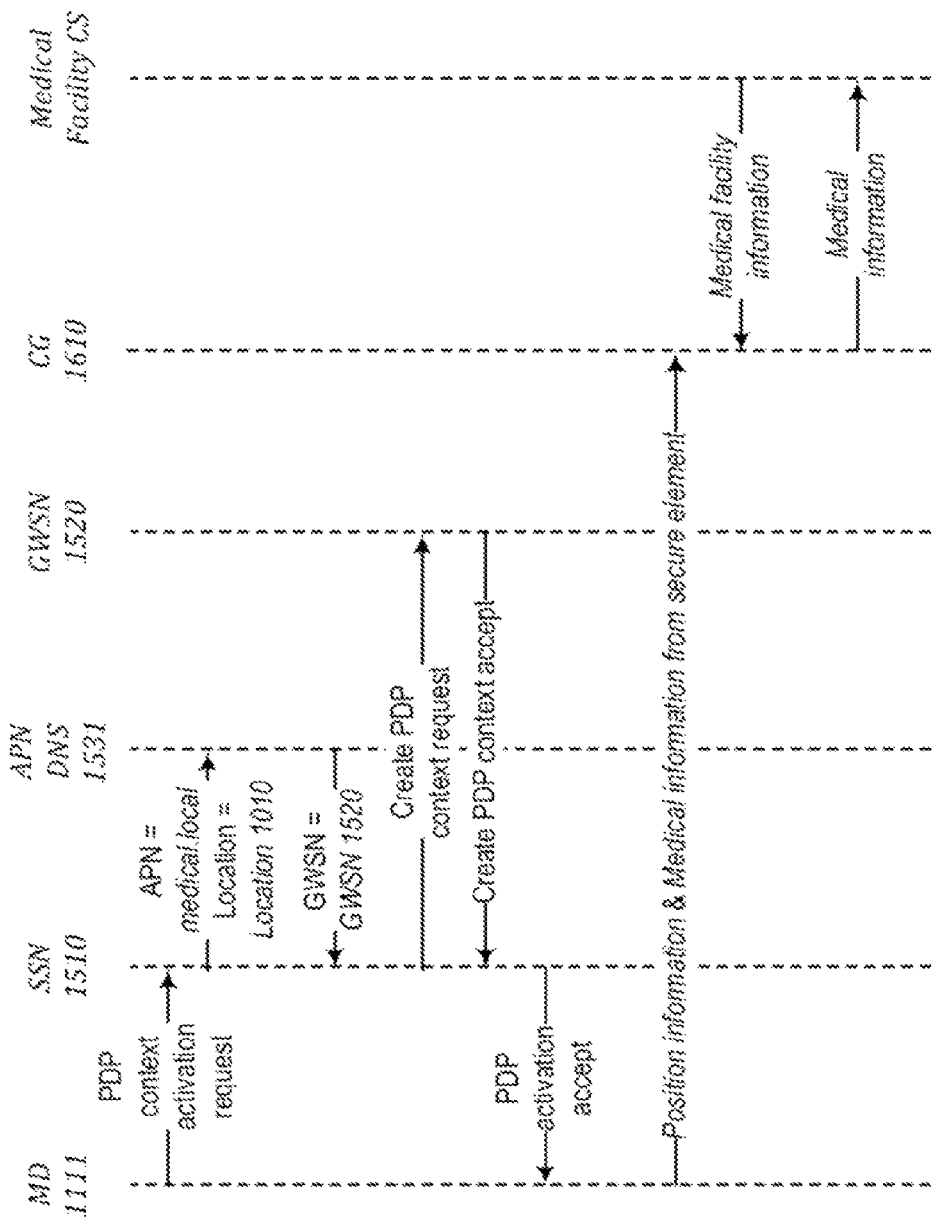
FIG. 2A illustrates an exemplary sequence diagram of utilizing a medical access point name from a first location, according to one or more embodiments.

In one example illustrated in an exemplary sequence diagram of FIG. 2A, MD 1111 can couple or attach to SSN 1510, via NB 1240 and RNC 1550, and can provide a packet data protocol (PDP) context activation request to SSN 1510. In one or more embodiments, the PDP context activation request can include a medical APN. For example, the medical APN can include an APN of "medical.local", "hospital", "office.doctor", "medical", "office.immediate-care.com", or "emergency.hospital.com", among others. In one or more embodiments, the PDP context activation request can include position information associated with MD 1111. For example, the position information associated with MD 1111 can include location data or a location identification (e.g., a cell ID). In one or more embodiments, when MD 1111 does not provide its position information, one or more systems of network 1410 can determine the position information associated with MD 1111 utilizing one or more methods and/or processes described herein.

In one or more embodiments, SSN 1510 can receive position information associated with MD 1111 and can query an APN DNS 1531 to determine a GWSN from two or more GWSNs, where the query can include the medical APN and the position information associated with MD 1111 (e.g., location data or a location identification associated with MD 1111). As illustrated, APN DNS 1531 can respond to the query with information indicating that the determined GWSN is GWSN 1520, and SSN 1510 can provide a create PDP context request that can be provided to GWSN 1520. For example, information indicating that the determined GWSN is GWSN 1520 can include a network address. For instance, the network address can be or include an IP address.

In one or more embodiments, the create PDP context request can include the medical APN and the position information associated with MD 1111. GWSN 1520 can receive and utilize the medical APN and/or the position information associated with MD 1111 in providing and/or permitting MD 1111 access to a coordination gateway (CG) 1610, coupled to SSN 1510. GWSN 1520 can accept the create PDP context request from SSN 1510, permit MD 1111 access of CG 1610, and, as shown, can respond to SSN 1510 with a create PDP context accept. As illustrated, SSN 1510 can send a PDP activation accept to MD 1111. In one or more embodiments, MD 1111 can utilize the PDP activation accept to determine that data communications with CG 1610 can be utilized.

As shown, CG 1610 can receive, from MD 1111, position information associated with MD 1111 and medical information associated with a user of MD 1111 and can receive medical facility information from at least one medical facility. In one or more embodiments, CG 1610 can receive medical facility information from multiple medical facilities (e.g., medical facilities 1810 and 1820), and CG 1610 can use that information in determining a medical facility to provide the medical information. For example, CG 1610 can store the medical information and can forward, as illustrated, the medical information to a medical facility computer system (e.g., medical facility CS 1710, medical facility CS 1720, etc.). In one or more embodiments, CG 1610 can receive position information from multiple medical facilities (e.g., medical facilities 1810 and 1820) and can use the position information from the multiple medical facilities in determining a medical facility to provide the medical information. For example, CG 1610 can determine a medical facility closest to the MD.

Figure 2B:
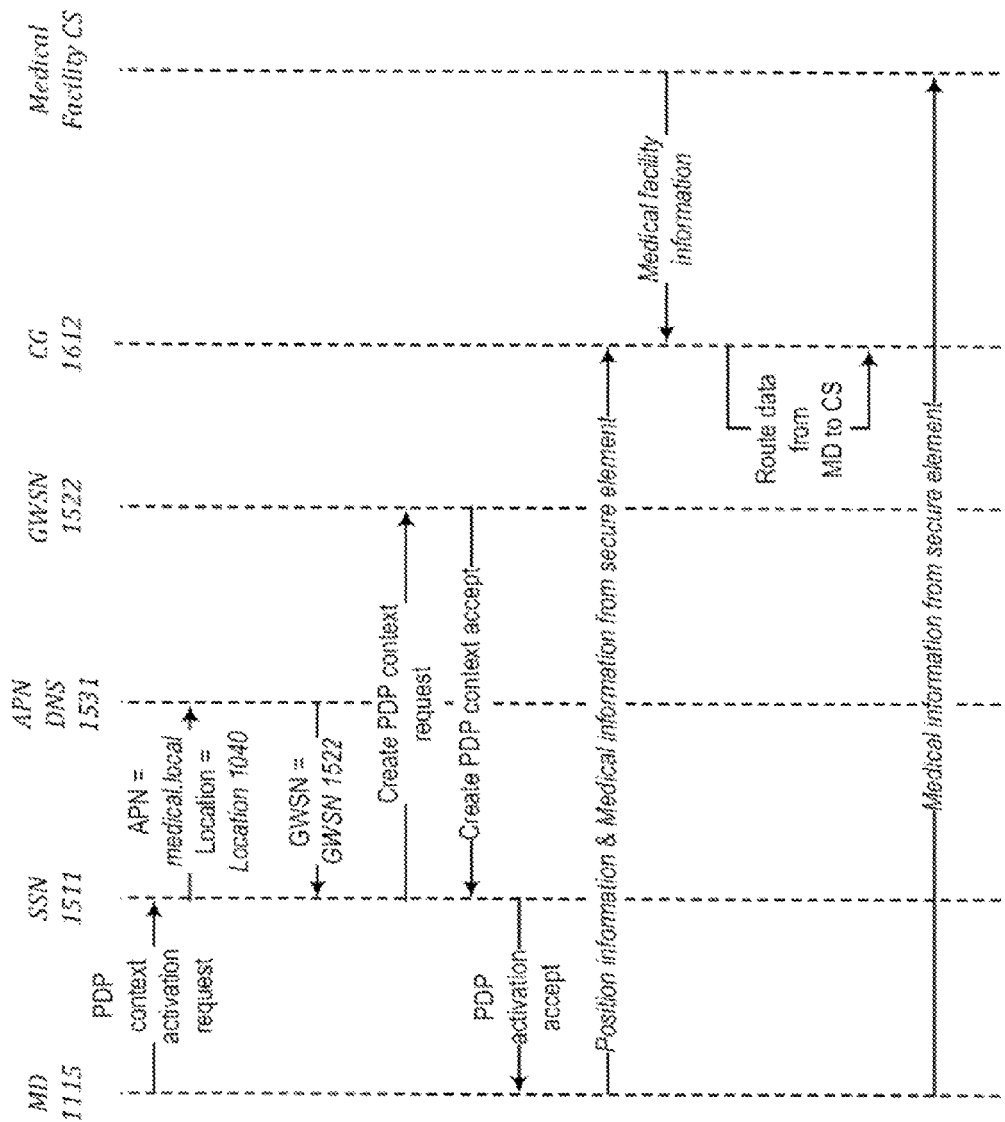
FIG. 2B illustrates an exemplary sequence diagram of utilizing a medical access point name from a second location, according to one or more embodiments.

In another example illustrated in an exemplary sequence diagram of FIG. 2B, MD 1115 can couple or attach to SSN 1511, via NB 1270 and RNC 1570, and can provide a PDP context activation request. In one or more embodiments, the PDP context activation request can include a medical APN. For example, the medical APN can include an APN of "medical.local", "hospital", "office.doctor", "medical", "office.immediate-care.com", or "emergency.hospital.com", among others. In one or more embodiments, the medical APN used by MD 1111 can be the same medical APN used by MD 1115. For example, the medical APN used by MD 1111 and MD 1115 can be "medical.local".

In one or more embodiments, the PDP context activation request can include position information associated with MD 1115. For example, the position information associated with MD 1115 can include location data or a location identification (e.g., a cell ID). In one or more embodiments, when MD 1111 does not provide its position information, one or more systems of network 1410 can determine the position information of MD 1115 utilizing one or more methods and/or processes described herein.

In one or more embodiments, SSN 1511 can receive position information associated with MD 1115 and can query an APN DNS 1531 to determine a GWSN from multiple GWSNs, where the query can include the medical APN and the position information associated with MD 1115 (e.g., location data or a location identification associated with MD 1115). As illustrated, APN DNS 1531 can respond to the query with information indicating that the determined GWSN is GWSN 1522, and SSN 1511 can provide a create PDP context request that can be provided to GWSN 1522. For example, information indicating that the determined GWSN is GWSN 1522 can include a network address. For instance, the network address can be or include an IP address.

In one or more embodiments, the create PDP context request can include the medical APN and the position information associated with MD 1115. GWSN 1522 can receive and utilize the medical APN and/or the position information associated with MD 1115 in providing and/or permitting MD 1115 access to a CG 1612, coupled to SSN 1511. GWSN 1520 can accept the create PDP context request from SSN 1511, permit MD 1115 access of CG 1612, and, as shown, can respond with a create PDP context accept. As illustrated, SSN 1511 can send a PDP activation accept to MD 1115. In one or more embodiments, MD 1115 can utilize the PDP activation accept to determine that data communications with CG 1612 can be utilized.

As shown, CG 1612 can receive position information and medical information from MD 1115 and can receive medical facility information. In one or more embodiments, CG 1612 can receive medical facility information from multiple medical facilities and/or position information from the multiple medical facilities, and CG 1612 can use the medical facility information from multiple medical facilities and/or position information from the multiple medical facilities in determining a medical facility to permit MD 1115 access. For example, CG 1612 can determine a medical facility to permit MD 1115 access that is closest to MD 1115. For instance, medical facility 1830 of location 1090 may be closer to MD 1115 than medical facility 1840 of location 1060. In one example, CG 1612 can permit routing of data from MD 1115 to medical facility CS 1730. For instance, MD 1115 can provide medical information to medical facility CS 1730 via CG 1612. In another example, CG 1612 can permit routing of data from MD 1115 from medical facility CS 1730.

In one or more embodiments, the one or more computer systems can determine that a MD is at a location (e.g., a location of locations 1010-1040) via one or more systems, methods, and/or processes. In one example, position information (e.g., latitude, longitude, altitude, etc.) of the MD can be determined using data from a global positioning system (GPS) device and/or mechanism of the MD. For instance, the GPS device and/or mechanism can be included in the MD, and the MD can communicate position information from the GPS device and/or mechanism to a SSN (e.g., SSN 1510, SSN 1511, etc.).

In a second example, the position information of the MD can be determined using a triangulation system, method, and/or process. For instance, at least three base transceiver stations can communicate with the MD, and strength of a signal and/or timing the signal propagation from the MD to the at least three cellular telephone antennas of one or more base transceiver stations can be used in determining the position information of the MD. In one or more embodiments, the location can be provided to the MD or a DNS such that the DNS can use the location in determining a network address in response to a query from the MD. For example, data associated with location 1020 can be provided to the SSN 1510 or MD 1112. For instance, the data associated with location 1020 can include one or more of a state, a city, a zip code, a base transceiver station identification, a street, a street number, a unit identifier (e.g., a suite identifier, a condominium identifier, an apartment identifier, etc.), a cell ID, latitude information, longitude information, and altitude information, among others.

In a third example, strength of a signal from the MD to an antenna of a base transceiver station can be used in determining the position information of the MD. For instance, the strength of the signal transmitted from the MD can be different from the strength of the signal received by the antenna, and a distance from the antenna can be determined based on a differenced in transmitted strength of the signal and received strength of the signal. For example, a computer system (e.g., a computer system of network 1410) can communicate a signal to the MD, where the signal includes information that indicates a first signal strength, and the MD can transmit one or more signals, at or close to the first signal strength, to network 1410. Network 1410 can receive, at a second signal strength, the one or more signals transmitted by the MD, where the second signal strength is less than the first signal strength due to path loss, terrain, etc. In one or more embodiments, determining the distance from the antenna can be based on determining a path loss attenuation factor.

In one or more embodiments, a data structure stored in a memory medium can include terrain and/or data clutter information that can be used in determining the distance from the antenna of a base transceiver station using a calculation based on the differenced in transmitted strength of the signal and received strength of the signal. In one or more embodiments, the vicinity of the antenna that can communicate with the MD can include a sector of an area or volume covered by the antenna associated with network 1410, and the set of one or more locations can include one or more locations within the sector.

In one or more embodiments, a GWSN can couple a MD to a CG, and the CG can determine a medical facility to couple to the MD. In one example, CG 1610 can determine a medical facility to couple to MD 1111 based on position information associated with MD 1111 and/or position information associated with the medical facility. For instance, the determined medical facility can be a medical facility that is closest to MD 1111. In a second example, CG 1610 can determine a medical facility to couple to MD 1111 based on medical information of a user of MD 1111. In a third example, CG 1610 can determine a medical facility to couple to MD 1111 based on information from one or more medical facilities. In one instance, information from a medical facility can include status information (e.g., taking trauma patients, not taking trauma patients, emergency room open, emergency room not open, no emergency room, surgery rooms available, surgeons available, magnetic resonance imaging available, etc.). In another instance, information from a medical facility can include specialty information (e.g., heart specialty, children specialty, etc.). In another example, CG 1610 can determine a medical facility to couple to MD 1111 based on a medical facility preference of a user of MD 1111.

In one or more embodiments, a CG coupling a MD to a medical facility can include permitting the MD to transfer medical information of a user of the MD to a computer system of the medical facility via the CG. In one example, CG 1610 can couple MD 1111 to a CS 1710 of a medical facility 1810, and MD 1111 can provide medical information of a user of MD 1111 to CS 1710 via CG 1610. In a second example, CG 1610 can couple MD 1114 to a CS 1730 of a medical facility 1830, and MD 1114 can provide medical information of a user of MD 1114 to CS 1730 via CG 1612. In one or more embodiments, providing the medical information of the user to the medical facility can allow the medical facility to prepare and/or provision for an arrival of the user.

Figure 3:
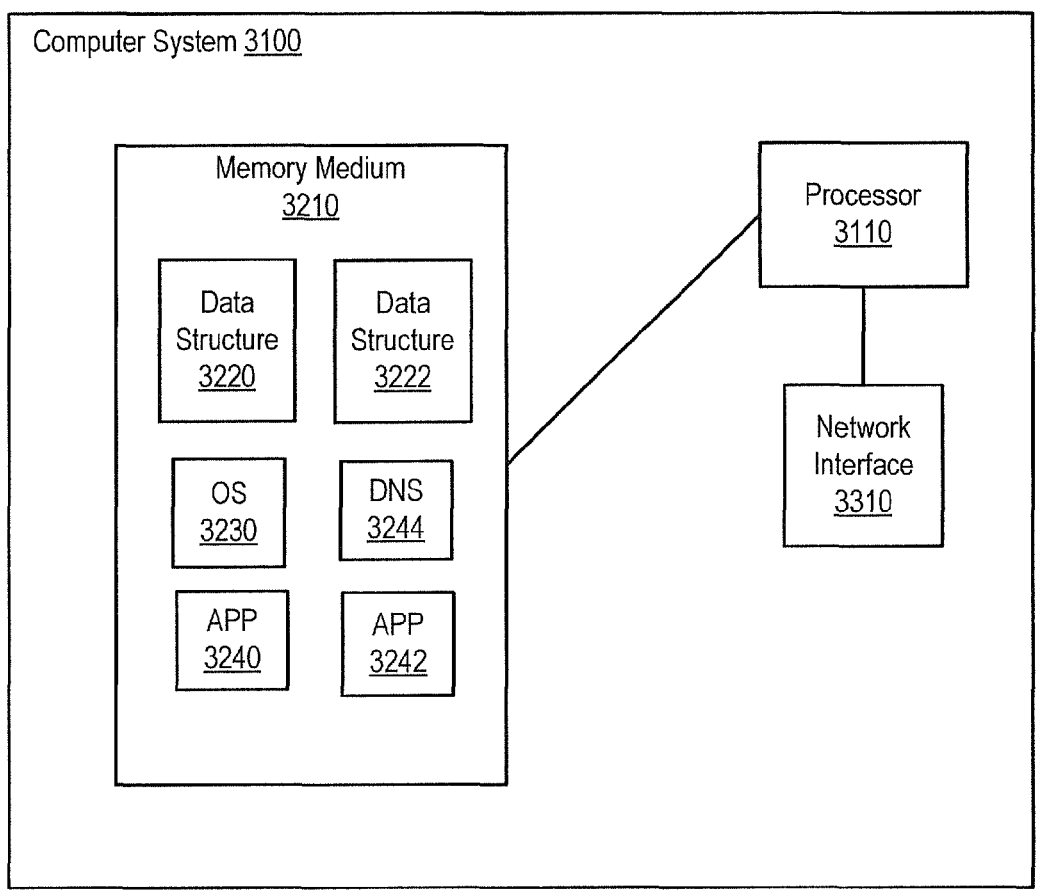
FIG. 3 provides block diagram of a computer system, according to one or more embodiments.

Turning now to FIG. 3, a block diagram of a computer system is illustrated, according to one or more embodiments. As shown, a CS 3100 can include a memory medium 3210 coupled to a processor 3110, and CS 3100 can include a network interface 3310. In one or more embodiments, memory medium 3210 can include one or more data structures 3220 and 3222, one or more applications (APPs) 3240 and 3242, a DNS 3244, and/or an operating system (OS) 3230 that can include instructions executable by processor 3110 and/or data in implementing one or more processes, methods, and/or systems described herein. In one or more embodiments, computer system 3100 may be any of various types of devices, including a server computer system, a networking appliance, and/or a core network server such as a home location register (HLR) or a home subscriber server (HSS), among others. In one or more embodiments, processor 3110 can include one or more cores, and each core of processor 3110 can implement an instruction set architecture (ISA). In one or more embodiments, one or more of computer systems 1710-1731 can include same or similar structures and/or functionality as described with reference to computer system 3100. In one or more embodiments, one or more of BTSes 1280 and 1290, BSC 1580, NBs 1240-1270, RNCs 1550-1570, APN DNSes 1530-1532, servicing support nodes (SSNs) 1510 and 1511, GWSNs 1520-1522, coordination gateways (CGs) 1610 and 1611 can include and/or can be implemented with one or more same or similar structures and/or functionality as described with reference to computer system 3100. For example, DNS 3244 can implement an APN DNS of APN DNSes 1530-1532.

Figure 4:
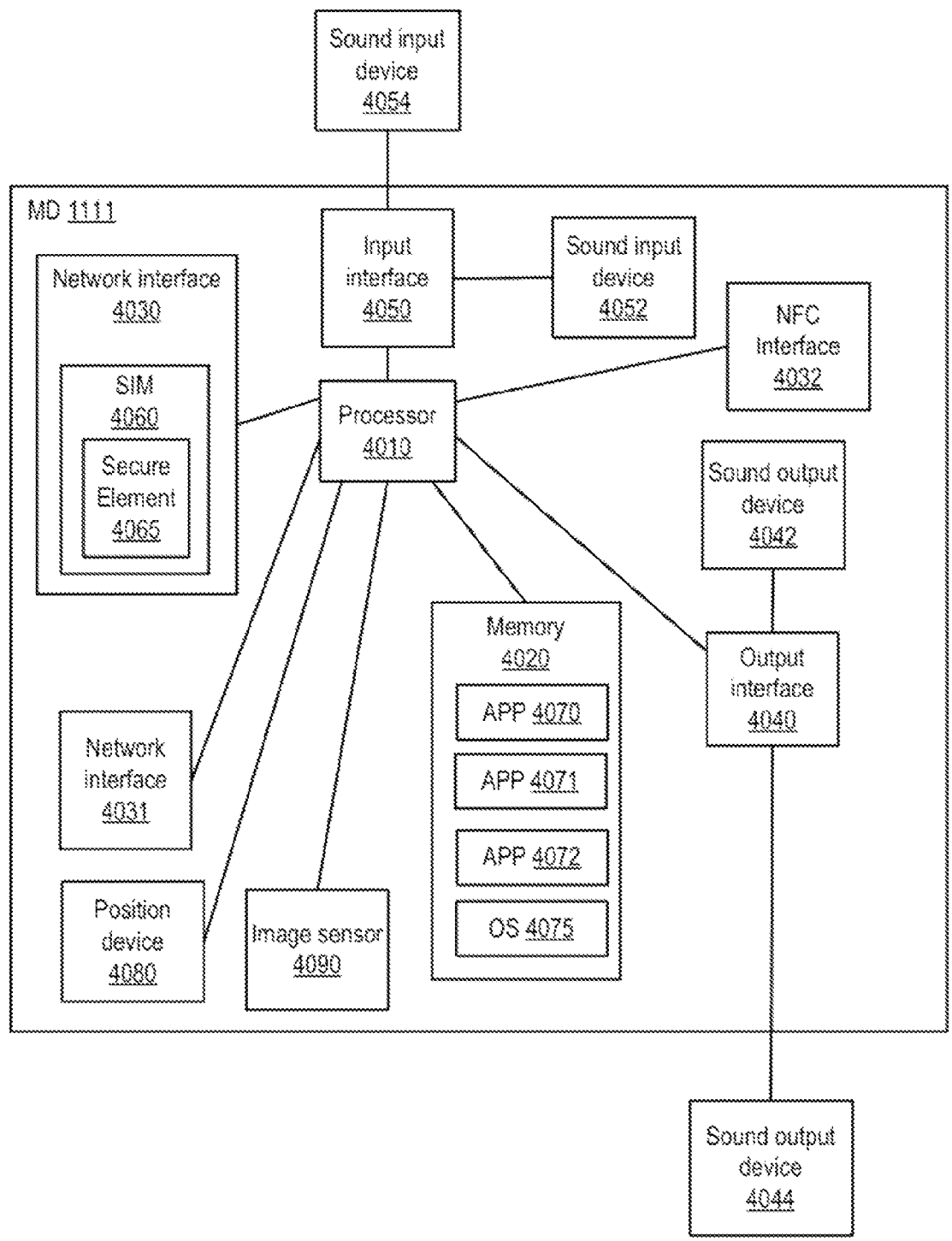
FIGS. 4 and 5 provide a block diagrams of a mobile device, according to one or more embodiments.
Figure 5:
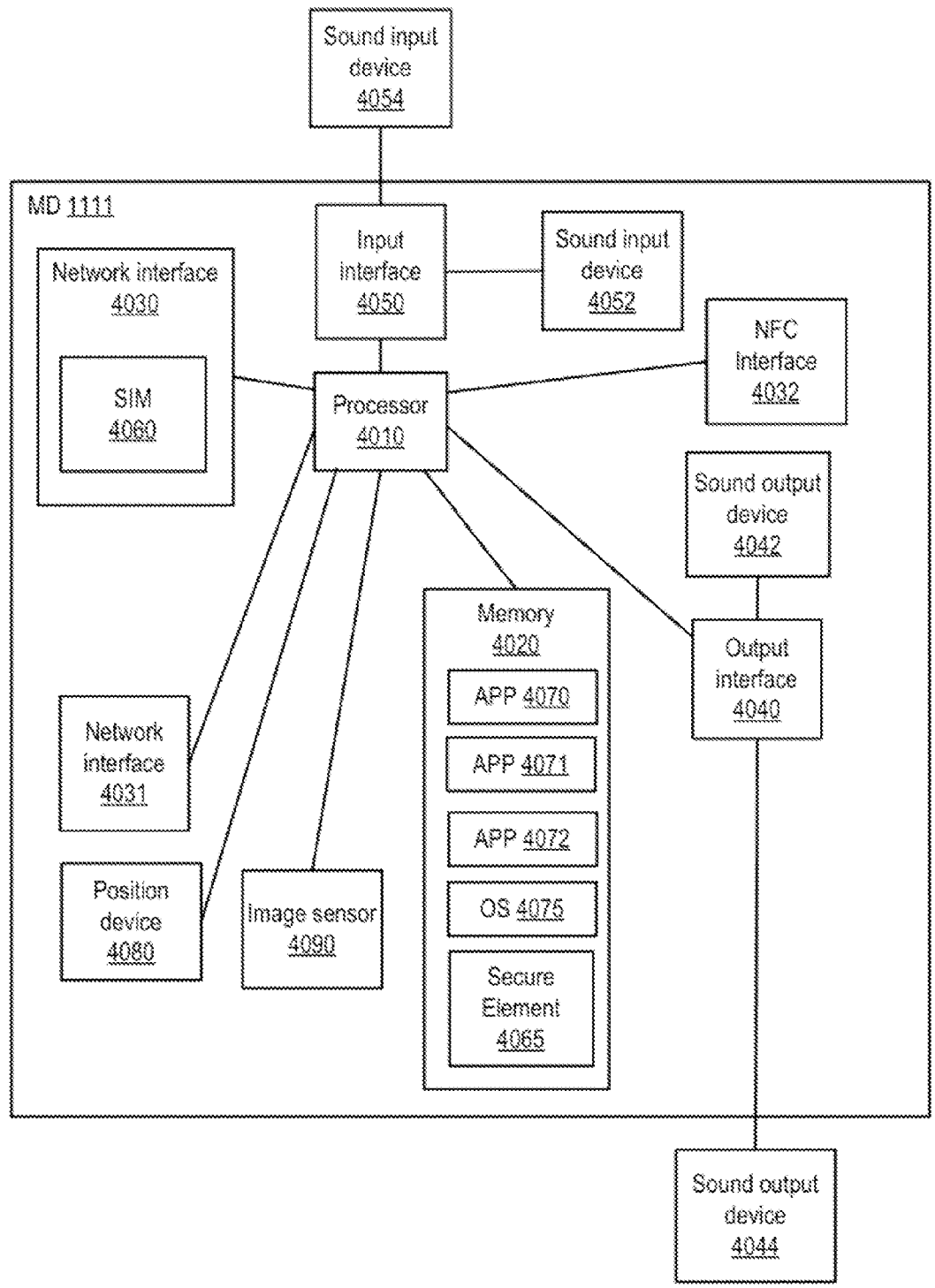

Turning now to FIGS. 4 and 5, block diagrams of a mobile device are illustrated, according to one or more embodiments.

As shown in FIG. 4, a subscriber identity module (SIM) 4060 can include a secure element 4065, and as shown in FIG. 5, a memory 4020 can include secure element 4065.

As illustrated in FIGS. 4 and 5, MD 1111 can include memory medium 4020 coupled to a processor 4010, and MD 1111 can include one or more network interfaces 4030 and 4031, a user output interface 4040, a user input interface 4050, a position device 4080, and an image sensor 4090, among others, coupled to processor 4010. In one or more embodiments, memory medium 4020 can include one or more APPs 4070-4072 and/or an OS 4075 that can include instructions executable by processor 4010 in implementing one or more methods, processes, and/or systems described herein. For example, APP 4070 can retrieve from secure element 4065 and/or store in secure element 4065 one or more of a medical APN and medical information of a user of MD 1111 in secure element 4065, which can store information in an encrypted fashion. For instance, APP 4070 can utilize an application programming interface (API) to retrieve from and/or store the medical information in secure element 4065. In one or more embodiments, one or more of APPs 4070-4072 can be installed before MD 1111 is distributed to a user, and/or one or more of APPs 4070-4072 can be installed and/or downloaded after MD 1111 is distributed to a user.

In one or more embodiments, processor 4010 can include one or more cores, and each core of processor 4010 can implement an ISA. In one or more embodiments, MD 1111 can be any of various types of devices. For example, MD 1111 can be or include a computer system, such as a portable computer, a tablet computing device, a personal digital assistant (PDA), a mobile telephone (e.g., a cellular telephone, a satellite telephone, etc.), a wearable computing device, an Internet appliance, a communications device, a handheld mobile computing device, or other wired or wireless device.

In one or more embodiments, user output interface 4040 can be used to convey information (e.g., text, graphic, video, haptic, audio, etc.) to a user of MD 1111. For example, MD 1111 may include a display (e.g., a display screen) that can be used to convey text, graphic, image, motion picture, and/or video information to a user of MD 1111. In one or more embodiments, MD 1111 can include a sound output device 4042 coupled to user output interface 4040. In one or more embodiments, sound output device 4042 can include a device and/or circuitry that can produce one or more sounds.

In one or more embodiments, user output interface 4040 can be coupled to a sound output device 4044. In one instance, sound output device 4044 can include one or more of an amplifier and/or a speaker. In another instance, sound output device 4044 can include one or more earphones. In one or more embodiments, user output interface 4040 can be coupled to sound output device 4044 in a wired fashion. In one or more embodiments, user output interface 4040 can be coupled to sound output device 4044 in a wireless fashion. In one example, user output interface 4040 can communicate sound information to output device 4044 using an ISM band. For instance, user output interface 4040 can communicate sound information to sound output device 4044 using one or more of a personal area network (PAN), IEEE 802.15, IEEE 802.15.4, ZigBee, 6LoWPAN, frequency modulation of a carrier wave, amplitude modulation of a carrier wave, light signals, and serial pulses, among others. In one or more embodiments, sound output device 4044 can be or be included in a device that includes an IEEE 802.15 receiver or transceiver, such as a Bluetooth headset or earpiece.

In one or more embodiments, user input interface 4050 can be used to receive sounds from a user of MD 1111. In one example, MD 1111 can include a sound input device 4052 coupled to user input interface 4050. In one instance, sound input device 4052 can include a microphone. In another example, a sound input device 4054 coupled to user input interface 4050. In one or more embodiments, a sound input device can include a device and/or circuitry that can receive one or more sounds and transform the one or more sounds into one or more electrical signals (e.g., voltage and/or current). In one or more embodiments, a sound input device can include an acoustic to electric transducer or sensor that can convert one or more sounds into one or more electrical signals. For example, the acoustic to electric transducer or sensor can include a body (e.g., a diaphragm, a crystal, a ceramic, etc.) that can vibrate in response to one or more sounds (e.g., in response to sound pressure), and movement of the body can be transformed and/or converted into one or more electrical signals. For instance, a sound input device can include a microphone. In one or more embodiments, a microphone can use one or more of capacitance change (e.g., a condenser microphone), electromagnetic induction (e.g., a dynamic microphone), piezoelectric generation, and light modulation to produce one or more electrical signal from one or more mechanical vibrations.

In one or more embodiments, user input interface 4050 can be coupled to sound input device 4054 in a wired fashion. In one or more embodiments, user input interface 4050 can be coupled to sound input device 4054 in a wireless fashion. In one example, user input interface 4050 can communicate sound information to sound input device 4054 using an ISM band. For instance, sound input device 4054 can communicate sound information to user input interface 4050 using one or more of a PAN, IEEE 802.15, IEEE 802.15.4, ZigBee, 6LoWPAN, frequency modulation of a carrier wave, amplitude modulation of a carrier wave, light signals, and serial pulses, among others. In one or more embodiments, sound input device 4054 can be or be included in a device that includes an IEEE 802.15 transmitter or transceiver, such as a Bluetooth headset or microphone.

In one or more embodiments, user input interface 4050 can be used to receive user input from a user of MD 1111. In one example, MD 1111 may include a keyboard that can be used to receive user input from a user of MD 1111. In another example, MD 1111 may include one or more sensors that can be used to receive user input from a user of MD 1111. In one instance, one or more sensors can include resistive sensors that can be used to determine one or more positions on a display screen. In another instance, one or more sensors can include capacitive sensors that can be used to determine one or more positions on a display screen. In one or more embodiments, user output interface 4040 and user input interface 4050 can be used in implementing a keyboard. For example, user output interface 4040 can be used to present an image of a keyboard, and user input interface 4050 can receive a position of user input on the image of the keyboard to determine a received key of the keyboard.

In one or more embodiments, network interface 4030 can include a transceiver that is operable to communicate information with network 1410. In one or more embodiments, network interface 4030 can be used to couple MD 1111 to network 1410, and MD 1111 can use network interface 4030 to communicate information (e.g., data, voice data, etc.) with network 1410. In one or more embodiments, network interface 4030 can include SIM 4060.

In one or more embodiments, SIM 4060 can securely store information associated with MD 1111 and/or a user of MD 1111. In one example, SIM 4060 can include and/or securely store secure element 4065 that can store medical information of the user of MD 1111. In another example, SIM 4060 can securely store an international mobile subscriber identity (IMSI) which can include a unique number and/or identity associated with a GSM network and/or an UMTS network, which can be or be included in network 1410. For instance, the unique number and/or identity can be used to determine information corresponding to MD 1111 from a HLR, a HSS, and/or from a visitor location register (VLR). In one or more embodiments, a MSISDN (mobile subscriber ISDN (integrated services digital network) number, mobile station international ISDN number(s), or mobile international ISDN number) can be a number that can uniquely identify a subscription in a GSM mobile network and/or a UMTS mobile network, which can be or be included in network 1410. For example, the MSISDN can include a telephone number corresponding to SIM 4060. In one instance, the MSISDN can include a country code, a national destination code, and a subscriber number. In another instance, the MSISDN can include a country code, a number planning area, and a subscriber number.

In one or more embodiments, SIM 4060 can be embodied in a removable card (e.g., a SIM card) that can be removed from a first MD associated with a first subscriber account and placed in a second MD, so that the second MD can be associated with the first subscriber account. For example, SIM 4060 embodied as a SIM card can be associated with a first subscriber account and used in MD 1111, thereby associating MD 1111 with the first subscriber account; SIM 4060 can be removed from MD 1111, thereby disassociating MD 1111 with the first subscriber account; and SIM 4060 can be placed in MD 1122, thereby associating MD 1122 with the first subscriber account.

In one or more embodiments, network interface 4031 can be used to communicate with one or more wireless APs. In one example, network interface 4031 can be configured and used to communicate with wireless AP 1210 in a wireless fashion. In one or more embodiments, network interface 4031 can include a transceiver that is operable to communicate information with one or more wireless APs.

As illustrated, MD 1111 can include a near field communication (NFC) interface 4032 coupled to processor 4010. In one or more embodiments, NFC interface 4032 can include one or more of a modulator, a demodulator, and an antenna, among others. In one or more embodiments, MD 1111 can utilize NFC interface 4032 in communications with a NFC terminal configured to be operated by medical personnel. For example, the medical personnel can use the NFC terminal to retrieve the medical information, of the user of MD 1111, stored in secure element 4065. For instance, APP 4070 receive a request for the medical information from the NFC terminal, authenticate the NFC terminal and/or the user of the NFC terminal, retrieve the medical information from secure element 4065, and provide the medical information to the NFC terminal. In one or more embodiments, MD 1111 and the NFC terminal can communicate in a secure fashion. For example, MD 1111 and the NFC terminal can communicate data using an encryption system, method, and/or process. For instance, MD 1111 can encrypt the medical information and provide the encrypted medical information to the NFC terminal. For example, the encrypted medical information can provide privacy for and/or authentication of the medical information.

In one or more embodiments, MD 1111 can include a position device 4080 coupled to processor 4010. In one example, position device 4080 can include a GPS receiver. In another example, position device 4080 can include a terrestrial radio navigation system receiver such as LORAN (LOng RAnge Navigation). In one or more embodiments, position device 4080 can provide one or more services such as one or more of positioning, navigation, and timing, among others, to processor 4010. For example, a positioning service can provide one or more of latitude information, longitude information, altitude information, and accuracy information (e.g., a radius of uncertainty for a geographic location or position).

In one or more embodiments, position device 4080 can provide heading information. For example, position device 4080 can include a compass and/or implement a compass to provide heading information. In one or more embodiments, position device 4080 can provide device position information such as tilt and/or angle information. For example, position device 4080 can include one or more of an accelerometer and an electronic gyroscope. In one or more embodiments, the compass can be electronically gimbaled using one or more of an accelerometer and an electronic gyroscope.

In one or more embodiments, electronic image sensor 4090 can provide digital data of one or more of an image, a motion picture, and a video. For example, electronic image sensor 4090 can be or include a digital camera. In one or more embodiments, the digital data of one or more of an image, a motion picture, and a video can include one or more formats. For example the one or more formats can include one or more of a tagged image file format (TIFF), a joint photographic experts group (JPEG) format, an exchangeable image file format (EXIF), a RAW format, a portable network graphics (PNG) format, a graphic interchange format (GIF), a bitmap (BMP) format, and a vector file format, among others.

Figures 6, 7A:
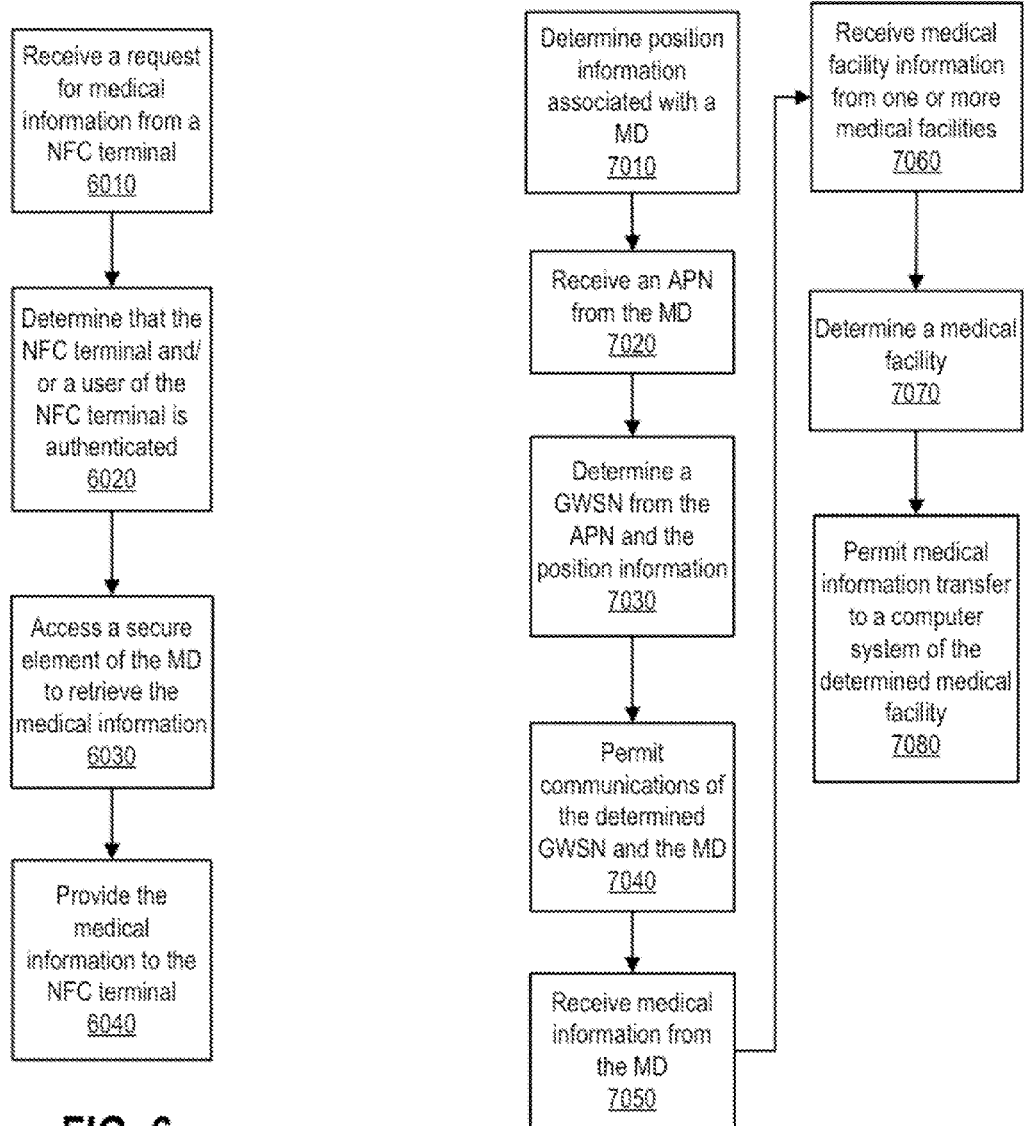
FIG. 6 provides a diagram of a method to provide medical information to a near field communication terminal, according to one or more embodiments.
FIG. 7A provides a diagram of a method to provide medical information to a computer system associated with a medical facility, according to one or more embodiments.

Turning now to FIG. 6, a method to provide medical information to a near field communication terminal is illustrated, according to one or more embodiments. At 6010, MD 1111 can receive a request for medical information from a NFC terminal. For example, MD 1111 can receive a request for medical information from a NFC terminal via NFC interface 4032. In one or more embodiments, the request for medical information from a NFC terminal via NFC interface 4032 can include or be included in a NFC handshake between NFC interface 4032 and the NFC terminal. At 6020, MD 1111 can determine that the NFC terminal and/or a user of the NFC terminal is authenticated. In one or more embodiments, MD 1111 can provide a query to the NFC terminal and/or the user of the NFC terminal and can determine that a response to the query authenticates the NFC terminal and/or the user of the NFC terminal. For example, a response to the query that authenticates the NFC terminal and/or the user of the NFC terminal can ensure, safeguard, and/or confirm that privacy of the medical information of the user of MD 1111 can be established and/or maintained.

At 6030, MD 1111 can access secure element 4065 to retrieve the medical information. In one or more embodiments, secure element 4065 can include an interface that is utilized to ensure, safeguard, and/or confirm that privacy of the medical information of the user of MD 1111 can be established and/or maintained. For example, APP 4070 can include and/or utilize an API to access secure element 4065 via the interface of secure element 4065. In one or more embodiments, secure element 4065 can store the medical information in a secured and/or encrypted fashion. For example, APP 4070 can include and/or utilize an API to access the medical information that is stored by secure element 4065 in secured and/or encrypted fashion.

At 6040, MD 1111 can provide the medical information to the NFC terminal. In one or more embodiments, MD 1111 and the NFC terminal can communicate in a secure fashion. For example, MD 1111 and the NFC terminal can communicate data using an encryption system, method, and/or process. For instance, MD 1111 can encrypt the medical information and provide the encrypted medical information to the NFC terminal. For example, the encrypted medical information can provide privacy for and/or authentication of the medical information.

Turning now to FIG. 7A, a method to provide medical information to a computer system associated with a medical facility is illustrated, according to one or more embodiments. At 7010, position information associated with a MD can be determined. In one example, position device 4080 can determine the position information associated with MD 1111, and network 1410 can receive the position information from the MD 1111. For instance, SSN 1510 can receive the position information from MD 1111.

In another example, one or more systems of network 1410 can determine the position information associated with MD 1111. In one instance, MD 1111 can be communicating with NB 1240, and one or more systems of network 1410 can determine that MD 1111 is at location 1010. In one or more embodiments, a memory medium can store a data structure that includes position information (e.g., latitude, longitude, altitude, etc.) and communications ranges associated with one or more NBs and/or sectors of NBs. For example, data structure 3220 can include position information and communications ranges of one or more of NBs 1240-1270 and/or BTSes 1280 and 1290. In one or more embodiments, data structure 3220 can be included in a database management system (DBMS) and/or can be accessed by other computer systems (e.g., computer systems 1715 and 1716) via a network. In one example, data structure 3220 can be included in a remote database management system (RDBMS) that can be accessed by other computer systems via a network. For instance, data structure 3220 can be included in a RDBMS such as Oracle, Microsoft SQL Server, MySQL, PostgreSQL, etc.

In one or more embodiments, a data structure that includes position information (e.g., latitude, longitude, altitude, etc.) associated with one or more NBs and/or BTSes can be distributed between or among two or more computer systems (e.g., computer systems 1715 and 1716). For example, the data structure that includes position information associated with the one or more NBs and/or BTSes can be distributed between or among two or more home location registers (HLRs), visitor location registers (VLRs), and/or home subscriber servers (HSSs). In one or more embodiments, a portion of the data structure that includes position information associated with the one or more NBs and/or BTSes can be duplicated. For example, a VLR can receive and/or store a portion of the data structure.

In another instance, MD 1114 can communicate with one or more of network 1410, a system associated with network 1410, and a system element associated with network 1410, among others, and one or more systems of network 1410 can determine that MD 1114 is at location 1040. In one or more embodiments, one or more systems can determine the position information associated with MD 1114 using a triangulation method and/or process. For example, at least three antennas of at least three respective base transceiver stations included in or coupled to network 1410 can receive one or more signals from MD 1114, and strength of the one or more signals and/or timing the signal propagation from MD 1114 to the at least three antennas of at least three respective base transceiver stations can be used in determining the position information.

In one or more embodiments, one or more systems of network 1410 can determine the position information of MD 1114 using a cell identification (cell ID or CID). In one example, a cell ID can include a unique identifier (e.g., a number, a string, etc.) that can be used to identify a base transceiver station communicating with MD 1114. In another example, a cell ID can include a unique identifier (e.g., a number, a string, etc.) that can be used to identify a sector of a base transceiver station communicating with MD 1114. In one instance, a last digit or character of a cell ID can represent a sector identification that can be used to identify the base transceiver station and the sector of the base transceiver station communicating with MD 1114. In one or more embodiments, data structure 3220 can include cell identifications (cell IDs or CIDs) with corresponding position information such that a first cell ID can be used to retrieve first position information corresponding to the first cell ID and a second cell ID can be used to retrieve second position information corresponding to the second cell ID.

In one or more embodiments, strength of a signal from MD 1114 to an antenna of a base transceiver station included in or coupled to the first network can be utilized in determining the position information associated with MD 1114. For example, a first strength of a signal transmitted from MD 1114 can be different from a second strength of the signal received by the antenna, and a distance from the antenna can be determined based on a difference in transmitted strength of the signal and received strength of the signal. For instance, the one or more computer systems can communicate a signal to MD 1114, where the signal includes information that indicates the first signal strength, and MD 1114 can transmit one or more signals, at or close to the first signal strength, to the first network. The first network can receive, at the second signal strength, the one or more signals transmitted by MD 1114, where the second signal strength is less than the first signal strength due to path loss, terrain, etc.

Since the first signal strength can depend on free space path loss, air path loss, terrain path loss (e.g., hills, valleys, mountains, vegetation, etc.), and/or structure path loss (e.g., buildings, bridges, towers, etc.), among others, a data structure that includes information associated with these dependencies can be utilized in determining a path loss attenuation factor and/or the position based on signal strength, according to one or more embodiments. In one or more embodiments, utilizing sector information associated with the first and second antennas and the data structure that includes information associated with one or more of free space path loss, air path loss, terrain path loss, and structure path loss can be used and/or aid in determining the differences in the distances by gauging the first and second received signal strengths with path loss information of the data structure.

In one or more embodiments, a vicinity of the antenna, that can communicate with a MD, can include a sector of an area or volume covered by the antenna, and the sector can be used in determining the position information. In one or more embodiments, determining the distance from the antenna can be used in determining the position information and/or can be based on determining a path loss attenuation factor. For example, path loss attenuation factor can be based on one or more of free space path loss, air path loss, terrain path loss, and structure path loss.

At 7020, an APN can be received from the MD. For example, a SSN can receive the APN from the MD, and the APN can be or include a medical APN. At 7030, a GWSN can be determine from the APN and the position information associated with the MD. For example, the SSN can provide the APN and the position information associated with the MD to an APN DNS, and the APN DNS can determine the GWSN, from multiple GWSNs (e.g., GWSNs 1520-1523), based on the APN and the position information associated with the MD. For instance, the APN DNS can determine a local medical GWSN based on a medical APN and position information associated with the MD.

At 7040, communications with the determined GWSN and the MD can be permitted. In one or more embodiments, permitting communications between the determined GWSN and the MD can include coupling the MD to the determined GWSN and/or establishing communications between the MD and the determined GWSN. In one example, coupling the MD to the determined GWSN can be performed after determining that the MD has been provisioned to use the APN. In another example, establishing communications between the MD and the determined GWSN can be performed after determining that the MD has been provisioned to use the APN.

At 7050, medical information associated with a user of the MD can be received. For example, a CG can receive the medical information. At 7060, medical facility information can be received from one or more medical facilities. For example, the CG can receive the medical facility information. At 7070, a medical facility can be determined.

At 7080, the medical information associated with the user of the MD can be permitted to be transferred to a computer system of the determined medical facility. In one example, the CG can provide the medical information associated with the user of the MD to the computer system of the determined medical facility. In another example, the CG can permit and/or provide data communications between the MD and the computer system of the determined medical facility. For instance, the computer system of the determined medical facility can receive, via the CG, the medical information associated with the user of the MD from the MD.

Figures 7B, 7C:
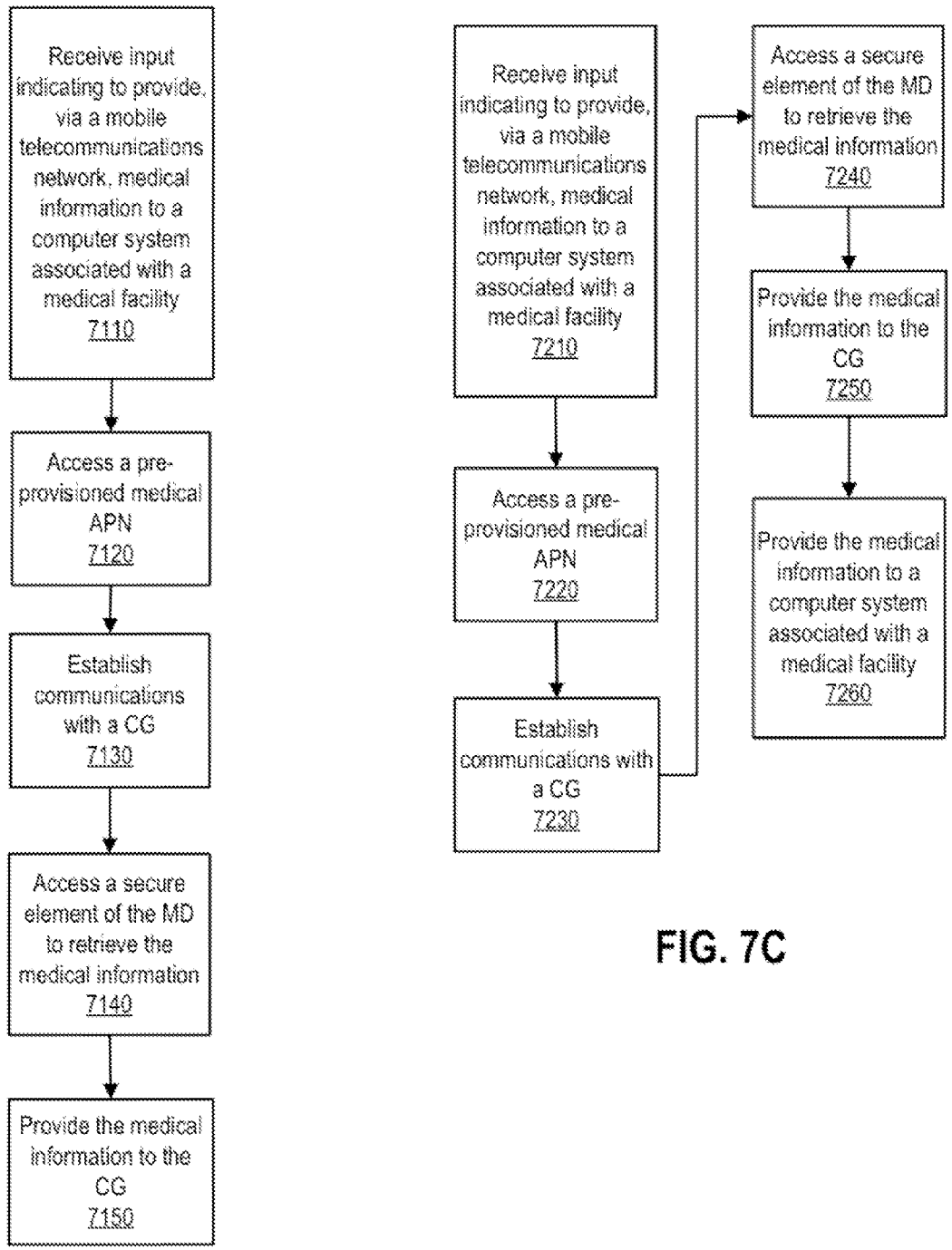
FIG. 7B provides a diagram of a method of operating a mobile device to provide medical information to a coordination gateway, according to one or more embodiments.
FIG. 7C provides a diagram of a method of operating a mobile device to provide medical information to a computer system associated with a medical facility, according to one or more embodiments.

Turning now to FIG. 7B, a method of operating a mobile device to provide medical information to a coordination gateway is illustrated, according to one or more embodiments. At 7110, a MD can receive input indicating to provide, via a mobile telecommunications network, medical information associated with a user of the MD to a computer system associated with a medical facility. At 7120, the MD can access a pre-provisioned medical APN. In one or more embodiments, the user of the MD may have subscribed to a service that provisioned used of the medical APN for use with the MD.

At 7130, the MD can establish communications with a CG. At 7040, the MD can access secure element 4065 to retrieve the medical information. In one or more embodiments, secure element 4065 can include an interface that is utilized to ensure, safeguard, and/or confirm that privacy of the medical information of the user of the MD can be established and/or maintained. For example, APP 4070 can include and/or utilize an API to access secure element 4065 via the interface of secure element 4065. In one or more embodiments, secure element 4065 can store the medical information in a secured and/or encrypted fashion. For example, APP 4070 can include and/or utilize an API to access the medical information that is stored by secure element 4065 in secured and/or encrypted fashion. At 7150, the MD can provide the medical information to the CG. In one or more embodiments, the CG can provide the medical information to a computer system associated with a medical facility.

Turning now to FIG. 7C, a method of operating a mobile device to provide medical information to a computer system associated with a medical facility is illustrated, according to one or more embodiments. In one or more embodiments, method elements 7210-7250 can be performed with reference to method elements 7110-7150 of FIG. 7B. In one or more embodiments, the CG can permit communications with a computer system of a medical facility. At 7260, the MD can provide, via the CG, the medical information to a computer system associated with a computer system of the medical facility.

For example, MD 1115 can provide, via CG 1612, the medical information to CS 1730. In one or more embodiments, MD 1115 and CS 1730 can communicate in a secure fashion. For example, MD 1115 and CS 1730 can communicate data using an encryption system, method, and/or process. For instance, MD 1115 can encrypt the medical information and provide the encrypted medical information to CS 1730 via CG 1612. For example, the encrypted medical information can provide privacy for and/or authentication of the medical information.

Turning now to FIGS. 8-12, multiple exemplary views of a graphical user interface are illustrated, according to one or more embodiments. As shown, a tab of tabs 8210-8218 of a graphical user interface (GUI) 8110 can be selected to display, access, and/or enter medical information via APP 4070. For example, a user of MD 1111 can select tabs 8210-8218 to display, access, and/or enter, respectively, a medical history, one or more medical conditions, physician contact information, emergency contact information, and one or more medical facility preferences. Information associated with tabs 8210-8218 are illustrated, respectively, in FIGS. 8-12.

Figure 8:
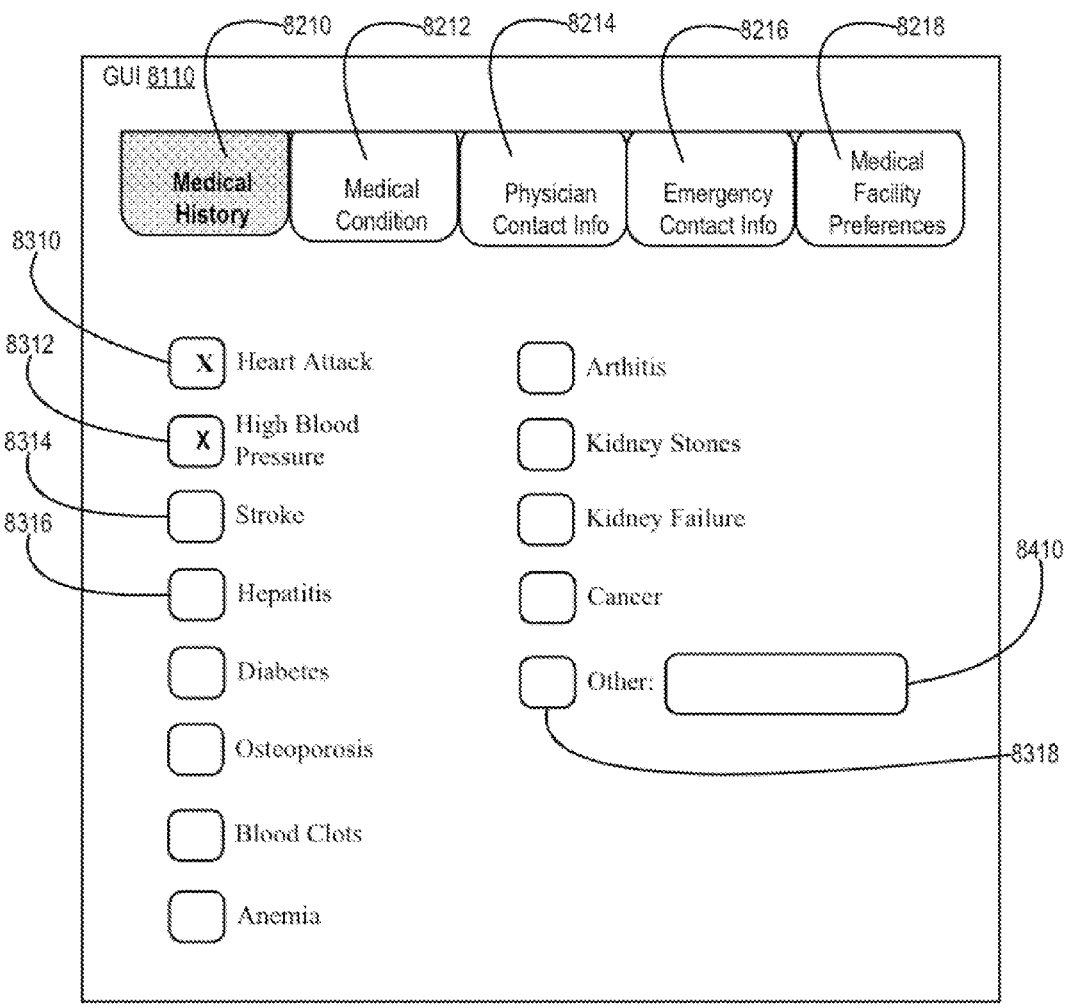
FIGS. 8-12 illustrate multiple exemplary views of a graphical user interface, according to one or more embodiments.

With reference to FIG. 8, one or more radio buttons or option buttons 8310-8318 can be selected by a user of MD 1111 via GUI 8110 of APP 4070. As shown, the user of MD 1111 can select buttons 8310 and 8312 to indicate a medical history of heart attack and high blood pressure, respectively. In one or more embodiments, the user of MD 1111 can select button 8318 to enter medical history information that is not listed. For example, medical history information can be entered via a text entry box or area 8410.

Figure 9:
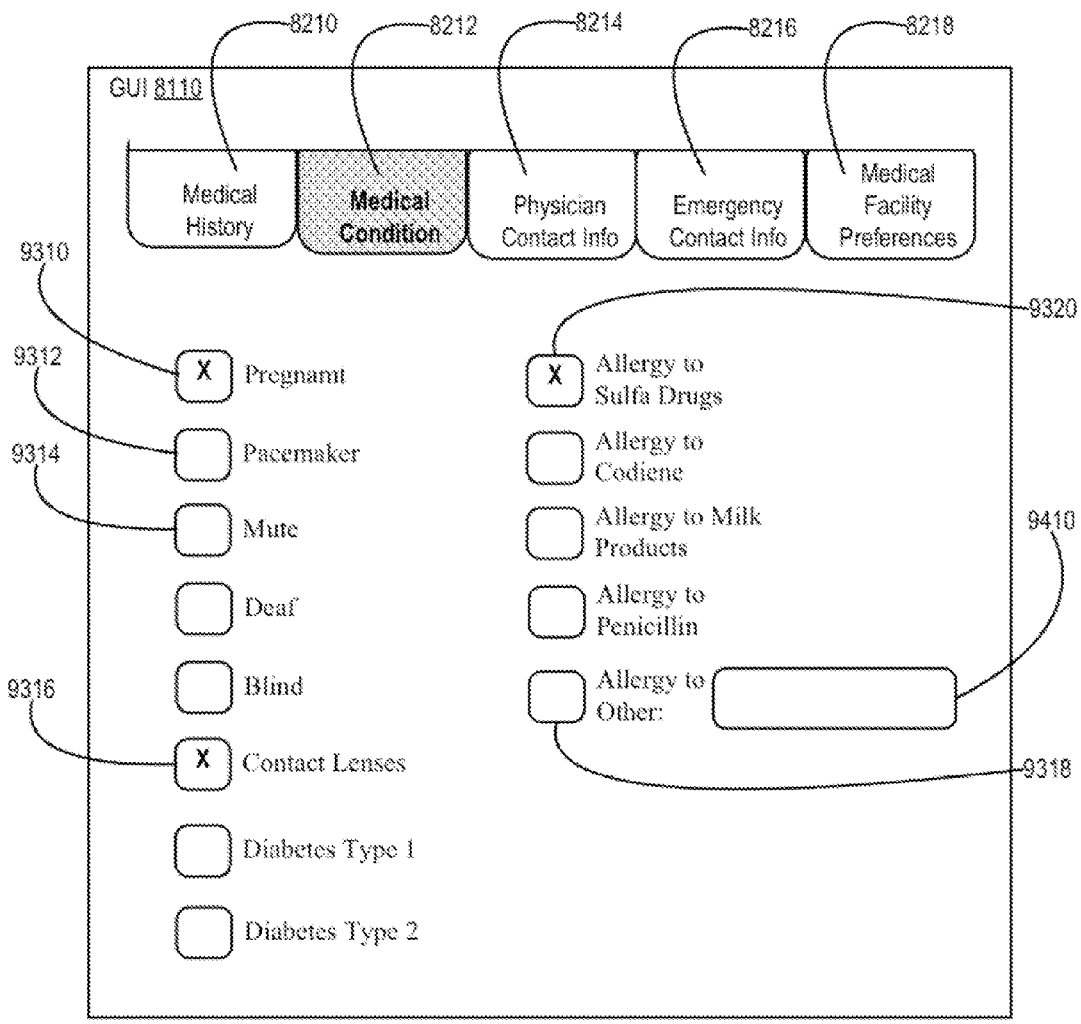

With reference to FIG. 9, one or more radio buttons or option buttons 9310-9320 can be selected by a user of MD 1111 via GUI 8110 of APP 4070. As shown, the user of MD 1111 can select buttons 9310, 9316, and 9320 to indicate a medical condition of being pregnant, wears contact lenses, and has an allergy to sulfa drugs, respectively. In one or more embodiments, the user of MD 1111 can select button 9318 to enter medical condition information that is not listed. For example, medical condition information can be entered via a text entry box or area 9410.

Figure 10:
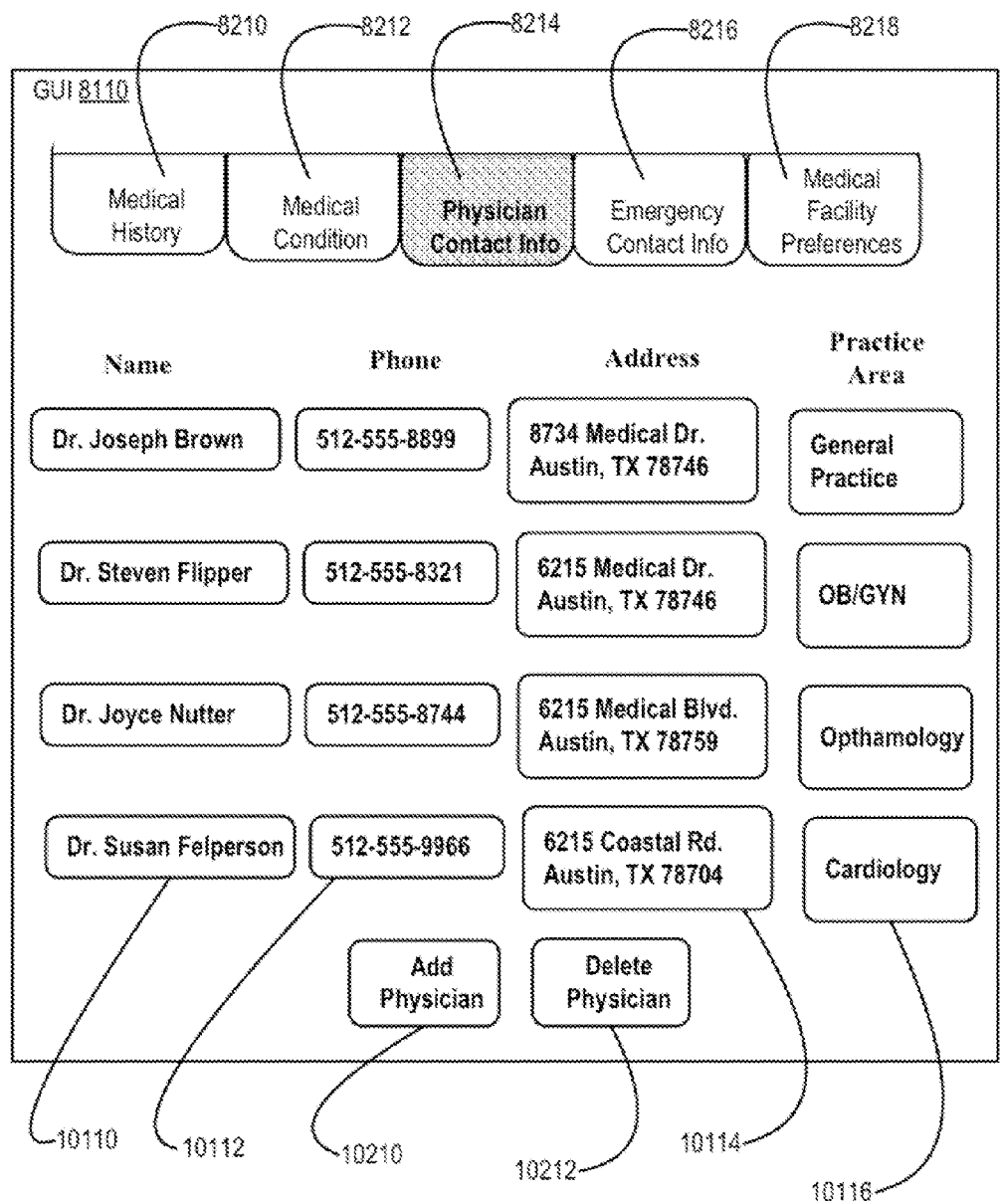

With reference to FIG. 10, a user of MD 1111 can, via GUI 8110 of APP 4070, display, access, and/or enter physician contact information. In one example, a user of MD 1111 can display, access, and/or enter physician contact information such as a name, a telephone number, an address, and a practice area via respective text entry boxes or areas 10110-10116. In another example, a user of MD 1111 can add new physician information and delete physician information via buttons or icons 10210 and 10212, respectively.

Figure 11:
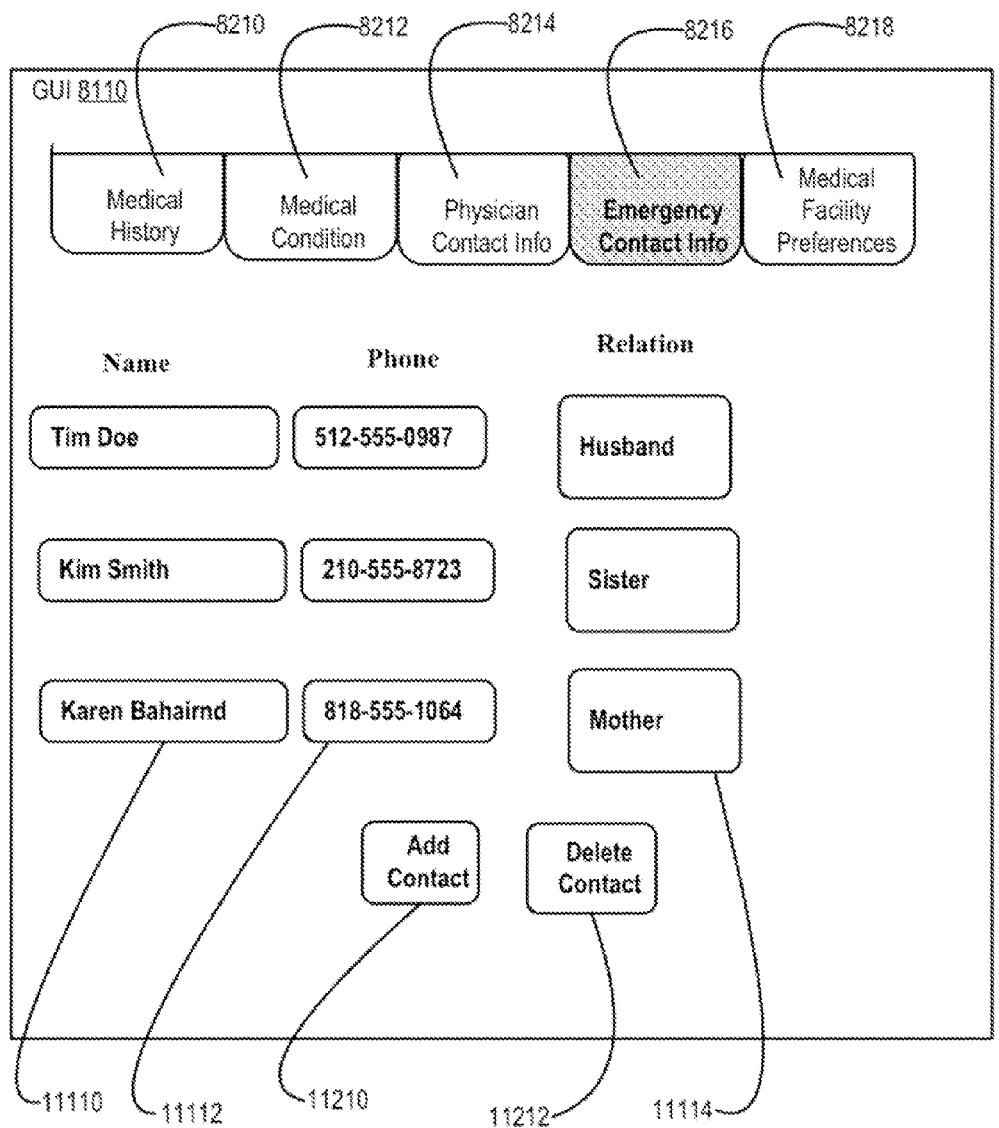

With reference to FIG. 11, a user of MD 1111 can, via GUI 8110 of APP 4070, display, access, and/or enter emergency contact information. In one example, a user of MD 1111 can display, access, and/or enter emergency contact information such as a name, a telephone number, and a relationship to the user via respective text entry boxes or areas 11110-11114. In another example, a user of MD 1111 can add new contact information and delete contact information via buttons or icons 11210 and 11212, respectively.

Figure 12:
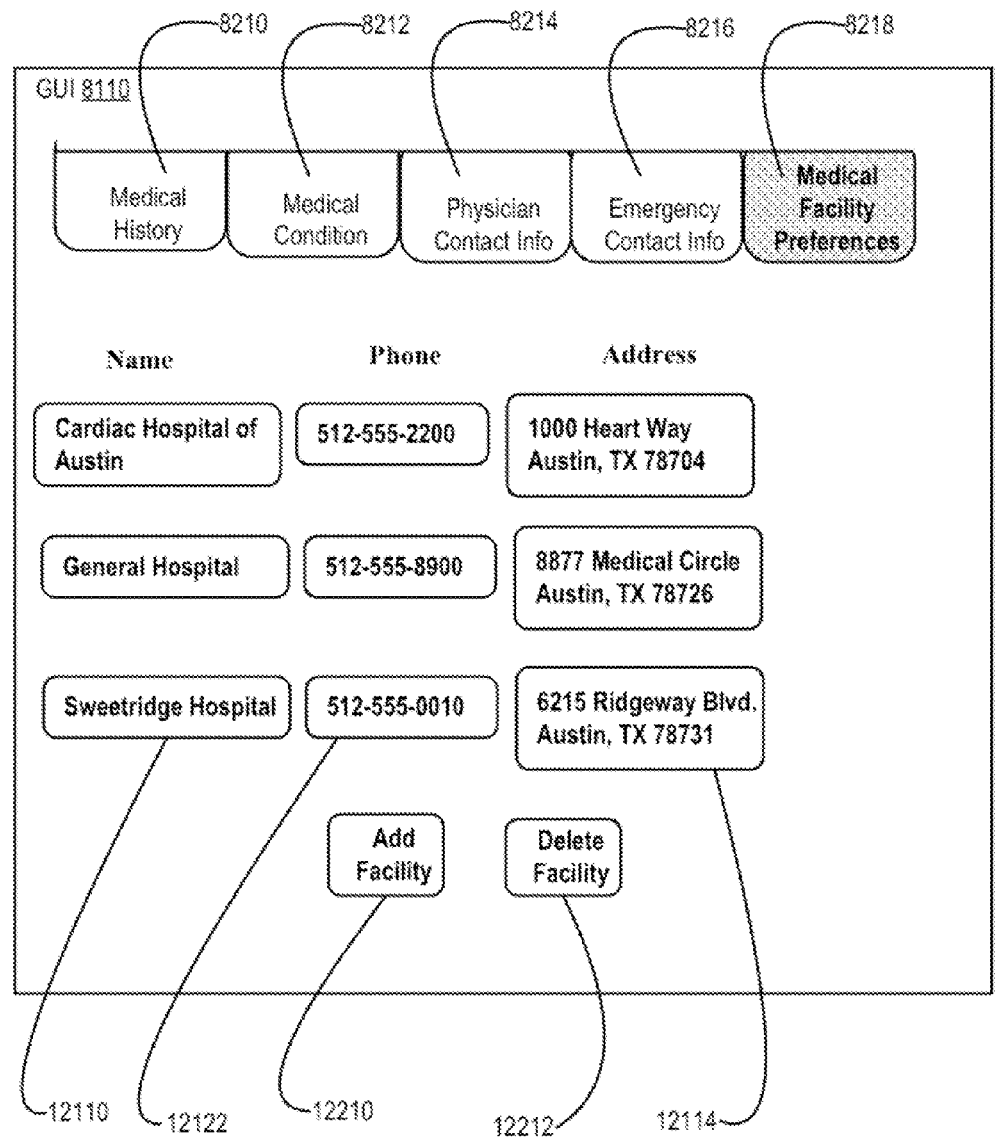

With reference to FIG. 12, a user of MD 1111 can, via GUI 8110 of APP 4070, display, access, and/or enter medical facility preference information. In one example, a user of MD 1111 can display, access, and/or enter medical facility preference information such as a name, a telephone number, and an address via respective text entry boxes or areas 12110-

12114. In another example, a user of MD 1111 can add new medical facility preference information and delete medical facility preference information via buttons or icons 12210 and 12212, respectively.

Figure 13:
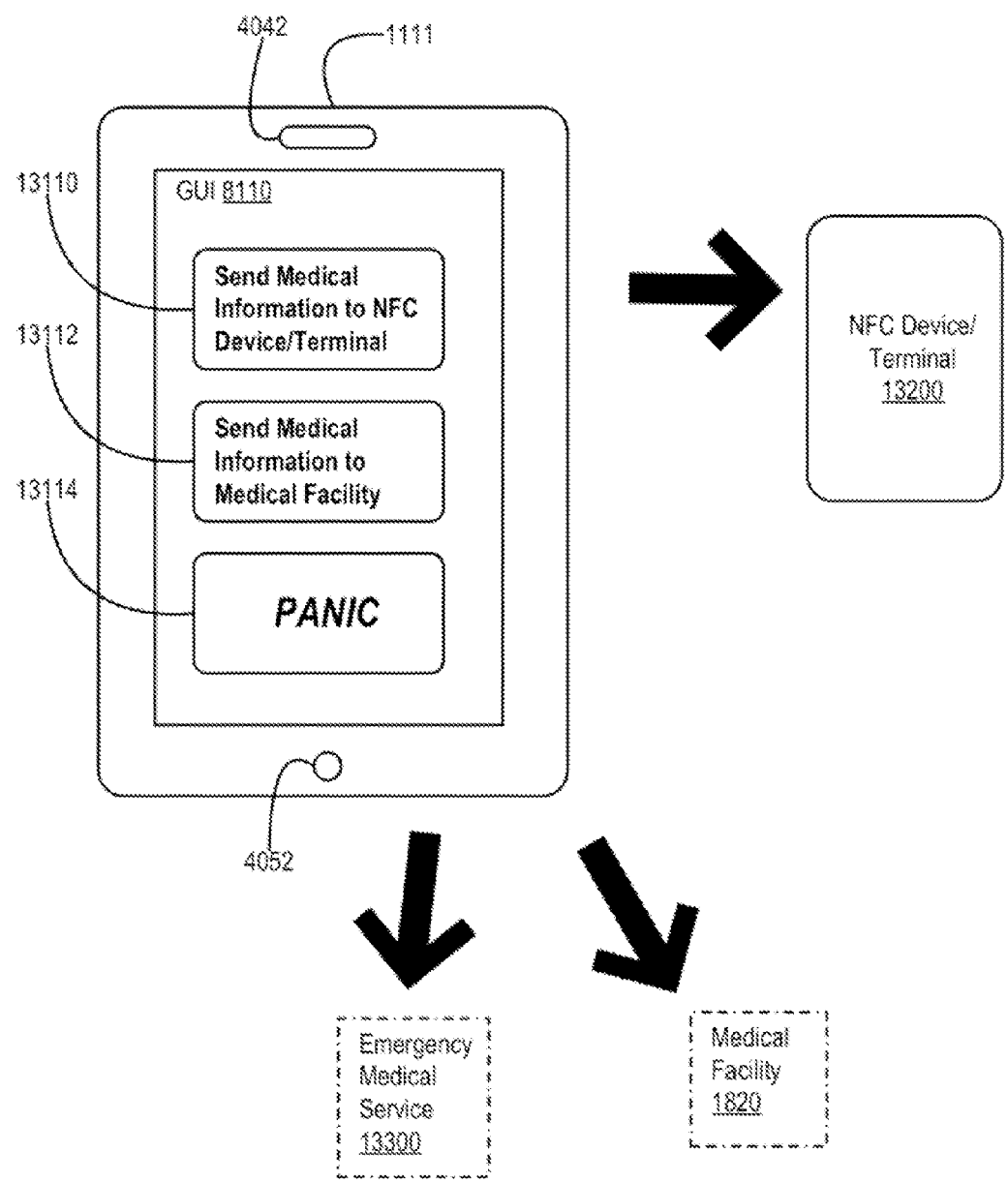
FIG. 13 provides a block diagram that illustrates options a user of a mobile device can utilize in sending medical information, according to one or more embodiments.

Turning now to FIG. 13, a block diagram that illustrates options a user of a mobile device can utilize in sending medical information is provided, according to one or more embodiments. As shown, GUI 8110 of APP 4070 can display and/or include buttons or icons 13110-13114 that can, respectively when actuated or selected, send the medical information of the user of MD 1111 to a NFC device or terminal 13200, send the medical information to a medical facility (e.g., medical facility 1820), and alert an emergency medical service 13300 and send the medical information to emergency medical service 13300. For example, emergency medical service 13300 can be or include a "911" emergency service.

In one or more embodiments, the term "memory medium" can mean a "memory" and/or "tangible computer readable medium" which is intended to include various types of memory or storage, including an installation medium, e.g., a CD-ROM, or floppy disks, a random access memory or computer system memory such as DRAM, SRAM, EDO RAM, Rambus RAM, NVRAM, EPROM, EEPROM, flash memory etc., and/or a non-volatile memory such as a magnetic media, e.g., a hard drive, and/or optical storage. The memory medium can include other types of memory as well, or combinations thereof. In one or more embodiments, the memory medium can be and/or include an article of manufacture and/or a software product that stores instructions executable by a processor in implementing one or more methods and/or processes described herein. In addition, the memory medium can be located in a first computer in which the programs are executed, or can be located in a second different computer and/or hardware memory device that connects to the first computer over a network. In one or more embodiments, the second computer provides the program instructions to the first computer for execution. The memory medium can also be a distributed memory medium, e.g., for security reasons, where a portion of the data is stored on one memory medium and the remaining portion of the data can be stored on a different memory medium. Also, the memory medium can include one of the networks to which the current network is coupled, e.g., a SAN (Storage Area Network), a NAS (Network Area Storage), a NFS (Network File System), etc.

In one or more embodiments, each of the systems described herein may take various forms, including a personal computer system, server computer system, workstation, network appliance, Internet appliance, wearable computing device, PDA, laptop, mobile telephone, mobile multimedia device, embedded computer system, television system, and/or other device. In general, the terms "processing system", "computing device", "computer", and/or "computer system" can be broadly defined to encompass any device having a processor which executes instructions from a memory medium. A CPU or processing unit in one or more systems executing code and data from a memory medium includes a means for executing one or more software program according to the methods and/or flowcharts described herein.

It is noted that, in one or more embodiments, one or more of the method elements described herein and/or one or more portions of an implementation of a method element can be performed in varying orders, can be repeated, can be performed concurrently with one or more of the other method elements and/or one or more portions of an implementation of a method element, or can be omitted. In one example, the methods of FIGS. 7A-7C can be repeated with different one or more mobile devices. Additional and/or duplicated method elements can be performed as desired. For example, a process and/or method can perform one or more described method elements concurrently with duplicates of the one or more described method elements. For instance, multiple methods, processes, and/or threads can be implemented using same described method elements.

In one or more embodiments, concurrently can mean simultaneously. In one or more embodiments, concurrently can mean apparently simultaneously according to some metric. For example, two or more method elements and/or two or more portions of an implementation of a method element can be performed such that they appear to be simultaneous to a human. It is also noted that, in one or more embodiments, one or more of the system elements described herein may be omitted and additional system elements can be added as desired.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system comprising:
a processor; and
a memory storing instructions that are executable by the processor to perform operations including:
receiving position information associated with a wireless mobile device,
receiving an access point name from the wireless mobile device;
identifying a particular gateway of a plurality of gateways for data communication with the wireless mobile device based on the position information and the access point name;
receiving medical information associated with a user of the wireless mobile device from the wireless mobile device; and
transmitting, via the particular gateway and a coordination gateway, the medical information to a particular computer system of a medical facility, wherein the particular computer system is identified based on the position information and the medical information.

2. The system of claim 1, further comprising:
the coordination gateway;
wherein the operations further include transmitting the medical information and the position information to the particular gateway, wherein the particular gateway provides the medical information to the particular computer system via the coordination gateway.

3. The system of claim 2, wherein the coordination gateway receives information from the particular computer system, and wherein the particular computer system is identified based on the information.

4. The system of claim 3, wherein the information includes a status of the medical facility, a specialty of the medical facility, or a combination thereof.

5. The system of claim 2, wherein the particular computer system is identified based on a medical facility preference included in the medical information.

6. The system of claim 2, wherein the coordination gateway receives the position information from the wireless mobile device, and wherein the wireless mobile device includes a global positioning system that determines the position information.

7. The system of claim 1, further comprising:
a base transceiver station that communicates with the wireless mobile device, wherein the base transceiver station is communicatively coupled to the processor;
wherein the position information is based on antenna position information of an antenna of the base transceiver station.

8. The system of claim 1, wherein the medical information includes a drug allergy, a food allergy, a health issue, physician contact information, emergency contact information, medication information, sex, age, height, weight, health insurance information, a preferred medical provider facility, a medical provider in an insurance network, an image of the user, or a combination thereof.

9. A method comprising:
determining, at a processor, first position information of a first wireless mobile device associated with a first user, wherein the first wireless mobile device stores first medical information associated with the first user;
receiving, at the processor, an access point name from the first wireless mobile device;
identifying, at the processor, a first gateway based on the first position information and the access point name;
receiving, at the processor, the first medical information from the first wireless mobile device; and
transmitting, via the first gateway and a first coordination gateway, the first medical information from the processor to a first computer system of a first medical facility, wherein the first computer system is identified based on the first position information and the first medical information.

10. The method of claim 9, further comprising:
determining, at the processor, second position information of a second wireless mobile device associated with a second user, wherein the second wireless mobile device stores second medical information associated with the second user; and
identifying, at the processor a second gateway based on the second position information and the access point name.

11. The method of claim 10, further comprising:
receiving, at the coordination gateway, first medical facility information from the first computer system of the first medical facility; and
enabling, at the processor, the first medical information to be provided to the first computer system via the coordination gateway;
wherein the first medical facility is identified based on the first medical facility information.

12. The method of claim 11, further comprising:
receiving, at the coordination gateway, the second medical information from the second wireless mobile device;
identifying, at the coordination gateway, a second medical facility based on the second position information and the second medical information, wherein the second medical facility is different from the first medical facility;
receiving, at the coordination gateway, second medical facility information from a second computer system of the second medical facility; and
enabling, at the processor, the second medical information to be provided to the second computer system via the coordination gateway;
wherein the second medical facility is identified based on the second medical facility information.

13. The method of claim 10, wherein the first medical information includes a first medical facility preference, and wherein the first medical facility is identified based on the first medical facility preference.

14. The method of claim 9, wherein determining the first position information includes receiving the first position information from the first wireless mobile device, and wherein the first wireless mobile device includes a global positioning system that determines the first position information.

15. The method of claim 10, wherein the first position information indicates a first city and the second position information indicates a second city that is different from the first city.

16. A mobile device comprising:
a processor;
a secure element in a memory that stores medical information associated with a user of the mobile device and provides the medical information to the processor; and
a first wireless interface that communicates with a wireless communication system;
wherein the memory stores instructions that are executable by the processor to perform operations including:
accessing the secure element;
retrieving a medical access point name from the secure element;
providing the medical access point name to a gateway of the wireless communication system via the first wireless interface, wherein the gateway is identified based on the medical access point name; and
transmitting the medical information to the gateway, wherein the gateway provides, via a coordination gateway, the medical information to a particular computer system of a medical facility, and wherein the particular computer system is identified based on the medical information and position information associated with the mobile device.

17. The mobile device of claim 16, wherein the operations further include:
retrieving, from the secure element, the medical infatuation associated with the user; and
providing the medical information to the gateway via the first wireless interface.

18. The mobile device of claim 16, further comprising:
a subscriber identification module coupled to the processor, wherein the subscriber identification module is associated with the secure element and an international mobile subscriber identity, a mobile subscriber integrated services digital network number, a mobile international integrated services digital network number, a subscriber telephone number, or a combination thereof.

19. The mobile device of claim 16, further comprising:
a global positioning system, coupled to the processor that determines the position information and provides the position information to the processor, wherein the operations further include providing the position information to the gateway via the first wireless interface.

20. The mobile device of claim 16, further comprising:
a second wireless interface, coupled to the processor, that communicates with a near field communication terminal via near field communications;

wherein the operations further include:
  authenticating the near field communication terminal via the second wireless interface; and
  providing the medical information to the near field communication terminal via the second wireless interface; and
wherein the medical information includes a drug allergy, a food allergy, a health issue, physician contact information, emergency contact information, medication information, sex, age, height, weight, health insurance information, a preferred medical provider facility, a medical provider in an insurance network, an image of the user, or a combination thereof.

* * * * *